US008814892B2

(12) United States Patent
Galdonik et al.

(10) Patent No.: US 8,814,892 B2
(45) Date of Patent: Aug. 26, 2014

(54) EMBOLECTOMY DEVICES AND METHODS FOR TREATMENT OF ACUTE ISCHEMIC STROKE CONDITION

(75) Inventors: Jason A. Galdonik, Hanover, MN (US); Grazyna Wlodarski, Andover, MN (US); John Kirchgessner, Saint Louis Park, MN (US); Kavitha Ganesan, Maple Grove, MN (US); Matthew F. Ogle, Fitchburg, WI (US)

(73) Assignee: Mivi Neuroscience LLC, Maple Grove, MN (US)

( * ) Notice: Subject to any disclaimer, the term of this patent is extended or adjusted under 35 U.S.C. 154(b) by 264 days.

(21) Appl. No.: 13/085,109

(22) Filed: Apr. 12, 2011

(65) Prior Publication Data

US 2011/0251629 A1 Oct. 13, 2011

Related U.S. Application Data

(60) Provisional application No. 61/323,461, filed on Apr. 13, 2010.

(51) Int. Cl.
*A61B 17/22* (2006.01)
*A61B 17/221* (2006.01)

(52) U.S. Cl.
CPC ..... *A61B 17/221* (2013.01); *A61B 2017/22044* (2013.01); *A61B 2017/22067* (2013.01); *A61B 2017/22094* (2013.01); *A61B 2017/22079* (2013.01)
USPC .......................................... 606/159; 606/200

(58) Field of Classification Search
CPC ......... A61F 2/01; A61F 2/013; A61B 17/221; A61B 17/3207; A61B 17/32056; A61B 17/320725
USPC ......... 606/108, 127, 128, 159, 200; 623/1.11, 623/1.12, 1.54
See application file for complete search history.

(56) References Cited

U.S. PATENT DOCUMENTS 4,610,662 A 9/1986 Weikl et al.
(Continued)

FOREIGN PATENT DOCUMENTS

WO 95/05209 A1 2/1995
(Continued)

OTHER PUBLICATIONS

Feldman, "Transcatheter Aspiration of a Thrombus in an Aortocoronary Saphenous Vein Graft," Am. J. Cardiol. 60(4):379-380 (1987).
(Continued)

*Primary Examiner* — Ashley Fishback
(74) *Attorney, Agent, or Firm* — Dardi & Herbert, PLLC; Peter S. Dardi; Kayla J. Fossen

(57) ABSTRACT

Clot engagement element comprising bundle of unwoven fibers can be assembled to form an acute stroke treatment device. The device has the capability of forming a three dimensional filtration matrix comprising effective pores with a distribution of sizes. The bundle of fiber design allows the device to be effectively delivered into circuitous cerebral arteries to remove clot that causes stroke. The fiber bundle based filtration matrix offers the advantages of conforming to the changing inner perimeter of a blood vessel during a clot removal process and thus the capability to effectively retain and remove a clot in the vessel. The filtration matrix offers the additional advantage to trap any break-off of the clot during the removal process. A plurality of fiber bundles can be combined to form an effective clot engagement element. Supplemental engagement structure as well as mechanical treatment structure can be integrated into the stroke treatment device. The deployment of the fiber based elements can be facilitated by actuation tool. Aspiration can be employed during the clot removal process.

32 Claims, 12 Drawing Sheets

(56) References Cited

U.S. PATENT DOCUMENTS

| | | |
|---|---|---|
| 4,723,549 A | 2/1988 | Wholey et al. |
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |
| 4,994,067 A | 2/1991 | Summers |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,163,906 A | 11/1992 | Ahmadi |
| 5,200,248 A | 4/1993 | Thompson et al. |
| 5,211,651 A | 5/1993 | Reger et al. |
| 5,462,529 A | 10/1995 | Simpson et al. |
| 5,549,626 A | 8/1996 | Miller et al. |
| 5,599,307 A | 2/1997 | Bacher et al. |
| 5,720,764 A | 2/1998 | Naderlinger |
| 5,766,191 A | 6/1998 | Trerotola |
| 5,810,874 A | 9/1998 | Lefebvre |
| 5,814,064 A | 9/1998 | Daniel et al. |
| 5,836,868 A | 11/1998 | Ressemann et al. |
| 5,843,051 A | 12/1998 | Adams et al. |
| 5,882,329 A | 3/1999 | Patterson et al. |
| 5,895,398 A | 4/1999 | Wensel et al. |
| 5,897,567 A | 4/1999 | Ressemann et al. |
| 5,902,263 A * | 5/1999 | Patterson et al. ............ 604/22 |
| 5,911,725 A | 6/1999 | Boury |
| 5,911,734 A | 6/1999 | Tsugita et al. |
| 5,935,139 A | 8/1999 | Bates |
| 5,938,645 A | 8/1999 | Gordon |
| 5,941,869 A | 8/1999 | Patterson et al. |
| 5,972,505 A | 10/1999 | Phillips et al. |
| 5,997,557 A | 12/1999 | Barbut et al. |
| 6,010,522 A | 1/2000 | Barbut et al. |
| 6,022,336 A | 2/2000 | Zadno-Azizi et al. |
| 6,066,149 A | 5/2000 | Samson et al. |
| 6,066,158 A | 5/2000 | Engelson et al. |
| 6,096,053 A | 8/2000 | Bates |
| 6,135,991 A | 10/2000 | Muni et al. |
| 6,142,987 A | 11/2000 | Tsugita |
| 6,159,195 A | 12/2000 | Ha et al. |
| 6,159,230 A | 12/2000 | Samuels |
| 6,160,084 A | 12/2000 | Langer et al. |
| 6,168,579 B1 | 1/2001 | Tsugita |
| 6,203,561 B1 | 3/2001 | Ramee et al. |
| 6,206,868 B1 | 3/2001 | Parodi |
| 6,238,412 B1 | 5/2001 | Dubrul et al. |
| 6,258,115 B1 | 7/2001 | Dubrul |
| 6,270,477 B1 | 8/2001 | Bagaoisan et al. |
| 6,270,513 B1 | 8/2001 | Tsugita et al. |
| 6,350,271 B1 | 2/2002 | Kurz et al. |
| 6,361,545 B1 | 3/2002 | Macoviak et al. |
| 6,391,045 B1 | 5/2002 | Kim et al. |
| 6,402,771 B1 | 6/2002 | Palmer et al. |
| 6,425,909 B1 | 7/2002 | Dieck et al. |
| 6,454,741 B1 | 9/2002 | Muni et al. |
| 6,458,139 B1 | 10/2002 | Palmer et al. |
| 6,475,477 B1 | 11/2002 | Kohn et al. |
| 6,485,500 B1 | 11/2002 | Kokish et al. |
| 6,511,492 B1 | 1/2003 | Rosenbluth et al. |
| 6,514,273 B1 | 2/2003 | Voss et al. |
| 6,544,276 B1 | 4/2003 | Azizi |
| 6,569,148 B2 | 5/2003 | Bagaoisan et al. |
| 6,592,607 B1 | 7/2003 | Palmer et al. |
| 6,596,011 B2 | 7/2003 | Johnson et al. |
| 6,610,077 B1 | 8/2003 | Hancock et al. |
| 6,620,148 B1 | 9/2003 | Tsugita |
| 6,632,236 B2 | 10/2003 | Hogendijk |
| 6,638,245 B2 | 10/2003 | Miller et al. |
| 6,641,590 B1 | 11/2003 | Palmer et al. |
| 6,660,021 B1 | 12/2003 | Palmer et al. |
| 6,663,650 B2 | 12/2003 | Sepetka et al. |
| 6,679,893 B1 | 1/2004 | Tran |
| 6,695,813 B1 | 2/2004 | Boyle et al. |
| 6,730,104 B1 | 5/2004 | Sepetka et al. |
| 6,746,468 B1 | 6/2004 | Sepetka et al. |
| 6,805,692 B2 | 10/2004 | Muni et al. |
| 6,824,545 B2 | 11/2004 | Sepetka et al. |
| 6,878,151 B2 | 4/2005 | Carrison et al. |
| 6,890,341 B2 | 5/2005 | Dieck et al. |
| 6,911,036 B2 | 6/2005 | Douk et al. |
| 6,986,778 B2 | 1/2006 | Zadno-Azizi |
| 7,029,488 B2 | 4/2006 | Schönholz et al. |
| 7,052,500 B2 | 5/2006 | Bashiri et al. |
| 7,058,456 B2 | 6/2006 | Pierce |
| 7,285,126 B2 | 10/2007 | Sepetka et al. |
| 7,344,550 B2 | 3/2008 | Carrison et al. |
| 7,534,252 B2 | 5/2009 | Sepetka et al. |
| 7,727,242 B2 | 6/2010 | Sepetka et al. |
| 7,727,243 B2 | 6/2010 | Sepetka et al. |
| 7,766,049 B2 | 8/2010 | Miller et al. |
| 7,766,921 B2 | 8/2010 | Sepetka et al. |
| 7,879,062 B2 | 2/2011 | Galdonik et al. |
| 7,931,659 B2 | 4/2011 | Bose et al. |
| 8,092,483 B2 | 1/2012 | Galdonik et al. |
| 2002/0022859 A1 | 2/2002 | Hogendijk |
| 2002/0035347 A1 | 3/2002 | Bagaoisan et al. |
| 2002/0169472 A1 | 11/2002 | Douk et al. |
| 2003/0023263 A1 | 1/2003 | Krolik et al. |
| 2003/0040762 A1 | 2/2003 | Dorros et al. |
| 2003/0078605 A1 | 4/2003 | Bashiri et al. |
| 2003/0135232 A1 | 7/2003 | Douk et al. |
| 2003/0163158 A1 | 8/2003 | White |
| 2004/0006365 A1 | 1/2004 | Brady et al. |
| 2004/0006367 A1 | 1/2004 | Johnson et al. |
| 2004/0049226 A1 | 3/2004 | Keegan et al. |
| 2004/0073243 A1 | 4/2004 | Sepetka et al. |
| 2004/0079429 A1 | 4/2004 | Miller et al. |
| 2004/0093015 A1 | 5/2004 | Ogle |
| 2004/0220611 A1 | 11/2004 | Ogle |
| 2005/0021075 A1 | 1/2005 | Bonnette et al. |
| 2005/0021152 A1 | 1/2005 | Ogle et al. |
| 2005/0033347 A1 | 2/2005 | Rauker et al. |
| 2005/0049619 A1 | 3/2005 | Sepetka et al. |
| 2005/0059995 A1 | 3/2005 | Sepetka et al. |
| 2005/0085847 A1 | 4/2005 | Galdonik et al. |
| 2005/0085848 A1 | 4/2005 | Johnson et al. |
| 2005/0085849 A1 | 4/2005 | Sepetka et al. |
| 2005/0209631 A1 | 9/2005 | Galdonik et al. |
| 2005/0277976 A1 | 12/2005 | Galdonik et al. |
| 2005/0288686 A1 | 12/2005 | Sepetka et al. |
| 2006/0058836 A1 | 3/2006 | Bose et al. |
| 2006/0189921 A1 | 8/2006 | Galdonik et al. |
| 2006/0195137 A1 | 8/2006 | Sepetka et al. |
| 2006/0200047 A1 | 9/2006 | Galdonik et al. |
| 2007/0038226 A1 | 2/2007 | Galdonik et al. |
| 2007/0060908 A1 | 3/2007 | Webster et al. |
| 2007/0060944 A1 | 3/2007 | Boldenow et al. |
| 2007/0172526 A1 | 7/2007 | Galdonik et al. |
| 2007/0198028 A1 | 8/2007 | Miloslavski et al. |
| 2007/0198076 A1* | 8/2007 | Hebert et al. ............ 623/1.11 |
| 2007/0208371 A1 | 9/2007 | French et al. |
| 2008/0082107 A1 | 4/2008 | Miller et al. |
| 2008/0172066 A9 | 7/2008 | Galdonik et al. |
| 2008/0234706 A1 | 9/2008 | Sepetka et al. |
| 2009/0105722 A1 | 4/2009 | Fulkerson et al. |
| 2009/0198269 A1 | 8/2009 | Hannes et al. |
| 2009/0306702 A1 | 12/2009 | Miloslavski et al. |
| 2010/0204672 A1 | 8/2010 | Lockhart et al. |

FOREIGN PATENT DOCUMENTS

| | | |
|---|---|---|
| WO | 98/38930 A1 | 9/1998 |
| WO | 02/02162 A2 | 1/2002 |
| WO | 02/055146 A1 | 7/2002 |
| WO | 02/085092 A2 | 10/2002 |

(56) References Cited

FOREIGN PATENT DOCUMENTS

| WO | 03/000334 A1 | 1/2003 |
| WO | 2005/000130 A1 | 1/2005 |
| WO | 2006/031410 A2 | 3/2006 |
| WO | 2007/117645 A2 | 10/2007 |
| WO | 2009/014723 A1 | 1/2009 |
| WO | 2010/010545 A1 | 1/2010 |

OTHER PUBLICATIONS

Nakagawa et al, "A Retrievable Nitinol Vena Cava Filter: Experimental and Initial Clinical Results," Journal of Vascular and Interventional Radiology 5:507-512 (1994).

Product brochure for Merci Retrieval System®, produced by Concentric Medical, Inc. 2010 (2 Pages).

* cited by examiner

EMBOLECTOMY DEVICES AND METHODS FOR TREATMENT OF ACUTE ISCHEMIC STROKE CONDITION

CROSS REFERENCE TO RELATED APPLICATIONS

This application claims priority to U.S. provisional patent application Ser. No. 61/323,461 filed on Apr. 13, 2010 to Jason Galdonik et al., entitled "Embolectomy devices and methods for treatment of acute ischemic stroke condition," incorporated herein by reference.

FIELD OF THE INVENTION

The inventions, in general, are related to acute stroke treatment devices used to remove clot in cerebral arteries. The inventions are further related to the method of using and making of such devices.

BACKGROUND

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction. To reduce the effects of the cut off in blood supply to the tissue, time is an important factor. In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries.

SUMMARY OF THE INVENTION

In a first aspect, the invention pertains to an acute stroke treatment device comprising one or more flexible delivery wires and a fiber-based clot engagement element that comprises at least one bundle of unwoven fibers and a first attachment element wherein each fiber of the bundle is secured at one end to the first attachment element. The first attachment element either comprises a slide that can translate over the delivery wire or an anchor that is secured at a fixed position around the circumference of the delivery wire. In some embodiments, if the first attachment element has an anchor fixed to the delivery wire, the other end of the fibers are unsecured or are secured in a bundle at a second attachment element without fixed attachment to an actuation structure, and the bundle of fibers have a first low profile delivery configuration and a second configuration with a portion of the fibers that is unsecured flaring outward relative to the delivery wire to have dimensions suitable for conform to the changing inner perimeter of a blood vessel and the fibers do not spontaneously transition between the first configuration and the second configuration.

In another aspect, the invention pertains to method for the delivery of a clot engagement device within a cerebral artery in which the method comprises the steps of positioning a distal opening of a guide catheter inside an interior carotid artery, delivering the clot engagement device through the guide catheter to access a cerebral artery downstream from the interior carotid artery, and advancing an actuation element over the flexible wire to deploy the fiber-based element to an extended configuration with the fibers conforming to the inner perimeter of the arteries. In general, the clot engagement device comprises a fiber-based clot engagement element supported by a flexible wire. Also, the movement of the actuation element can be unconstrained over the flexible wire.

In a further aspect, the invention pertains to method for the removal of a blood clot from a cerebral artery causing an acute stroke event, the method comprising the steps of positioning of a fiber-based clot engagement device inside the cerebral artery distal to the blood clot on a delivery wire, deploying the fiber-based clot engagement device to an extended configuration with at least a portion of the fibers extending outward relative to the delivery wire to conform to the inner perimeter of the cerebral artery, pulling the deployed clot engagement device towards an aspiration catheter positioned inside an interior carotid artery so the clot engagement device becomes engaged with the clot, and applying aspiration through the aspiration catheter while drawing the clot into the aspiration catheter with proximal movement of the clot engagement device. In some embodiments, the fibers of the clot engagement device remain conforming to the changing inner perimeter of the arteries and thereby remain engaging the clot during the pulling process.

BRIEF DESCRIPTION OF THE DRAWINGS

FIG. 7(a) is a photograph of a push catheter with a filament cartridge as a deployment tool in a deployed configuration.

FIG. 7(b) is a fragmentary side view of the push catheter with the filament cartridge of FIG. 7(a) in combination with a filter element in a narrow profile delivery configuration.

FIG. 7(c) is a schematic diagram showing the device of FIG. 7(b) in a narrow profile delivery configuration with the push catheter and the filament cartridge inside a microcatheter and the filter element extended outside the microcatheter with the insert showing an alternative embodiment of the push catheter with an open woven structure.

FIG. 7(d) is a schematic diagram showing the device of FIG. 7(c) with the filament cartridge advanced outside of the microcatheter in a deployed extended configuration.

FIG. 7(e) is a schematic diagram showing the device of FIG. 7(d) with the push catheter and the extended filament cartridge helping to deploy the filter element into an extended configuration.

DETAILED DESCRIPTION OF PREFERRED EMBODIMENTS

Figure 1:
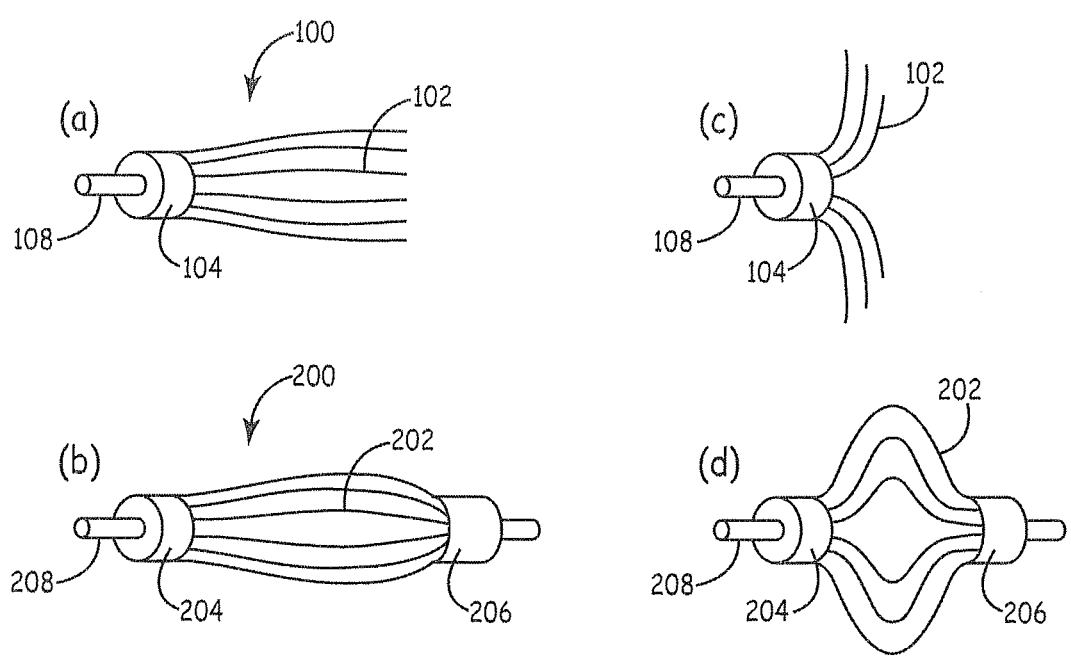
FIG. 1(a) is a side perspective view of a fiber cartridge with a bundle of fibers having a single fixed end.
FIG. 1(b) is a side perspective view of a fiber cartridge with a bundle of fibers having both ends fixed.
FIG. 1(c) is a side perspective view of the fiber cartridge of FIG. 1(a) with the non-secured end of the fibers flare outward in an extended deployed configuration.
FIG. 1(d) is a side perspective view of the fiber cartridge of FIG. 1(b) with the non-constrained middle portion of the fibers flare outward in an extended deployed configuration.

Improved cerebral embolectomy devices have been designed that can navigate through the circuitous paths of the cerebral arteries to a clot and to pass the clot with a fiber-based clot engagement element. To allow for the devices to navigate the circuitous path, the devices are based on a flexible wire that engages with fiber-based elements. A separate deployment device is used to track over the flexible wire after the distal end of the device is positioned past the clot to deploy the fiber based elements into an extended position, which may conform to the vessel wall around its inner perimeter. Embolectomy procedures for the treatment of acute stroke conditions involve navigating the cerebral embolectomy device along the tortuous path of cerebral arteries such that the device is positioned distal to the clot or emboli. The device is then deployed to pull the clot or emboli to a retrieval catheter, which can be an aspiration catheter. In some embodiments, the retrieval catheter has its distal end in the interior carotid artery. The cerebral embolectomy device generally comprises fibers that are designed for extending radially outward to contact the walls of the vessel to form a matrix. In some embodiments, the fiber matrix is designed to maintain contact with the vessel walls as the clot is pushed through the vessels with the vessels naturally undergoing significant increase in the vessel inner diameter if pushed a significant distance relative to the vessel structure.

Due to the circuitous nature of the cerebral arteries, the devices intended for placement up the cerebral arteries are designed for a high degree of flexibility and maneuverability. The fiber structures generally have a lower profile initial configuration and a larger profile extended configuration. The fiber structure can be supplemented with an element having a greater mechanical strength to facilitate the dislodgement of the clot. This supplemental structural element can be formed from wire and/or a thicker fiber. In additional or alternative embodiments, mechanical treatment devices, such as balloon or stents can be delivered over a flexible wire supporting the fiber-based structure to facilitate removal of the clot. Suction generally is applied through the retrieval catheter to facilitate removal of the clot from the vessel. The improved devices and corresponding procedures are designed for a high success rate with a low risk of losing portions of the clot as emboli can migrate downstream.

To reduce the clinical effects of a clot within a cerebral artery, the clot can be removed, and it is correspondingly desirable to keep the time for removal short. For convenience, as used herein all arteries downstream from the interior carotid arteries are referred to as a cerebral artery. The process of removal of the clot poses the challenge of tracking a device to the clot and physically engaging the clot to remove it. For at least a portion of the removal process, the clot can be drawn into a catheter or sheath to facilitate retention of the clot. Any portions of the clot that remains in the vessel or breaks off from the original clot can eventually flow downstream to block a smaller vessel with associated harm to the patient. The placement of a cerebral embolectomy device within a cerebral artery poses significant challenges due to the circuitous path through the vessels.

Fiber based devices have been found to result in surprisingly effective filtering within blood vessels. These devices can comprise a fiber mat formed of the fibers in a deployed configuration such that the fiber mat has the structure of a three dimensional filtration matrix. The three dimensional filtration matrix comprises effective pores with a distribution of sizes within the matrix. The pores with various sizes inside the matrix provide complex flow passages through the fiber mat to allow blood to pass through while effective retain emboli of various sizes. In some embodiments, the fibers are configured to be a non-woven bundle. Even after the deployment and formation of the fiber mat, the fibers remain unwoven. Filters formed from fiber bundles are described further in U.S. Pat. No. 7,879,062 to Galdonik et al., entitled "Fiber Based Embolism Protection Device," incorporated herein by reference.

In some embodiments, it can be desirable for a deployed fiber-based element(s) within a device to block the flow of a substantial majority of particulates with a diameter of at least about 0.2 mm while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A substantial majority of particulates can be considered to be at least about 90 percent and in further embodiments at least about 95 percent of all the particulates flown through. A person of ordinary skill in the art will recognize that additional ranges of filtering ability within the explicit ranges are contemplated and are within the present disclosure.

As discussed in further details below, with proper designs, the fiber-based filter elements can be very effective at trapping emboli generated during a procedure within a vessel while maintaining flow substantially unchanged through the filter. It has been found that in a modified form, fiber-based structures can be used effectively as cerebral embolectomy devices. The extended fibers can engage the clot and assist in the removal of the clot. The filtration character can provide advantageously the ability to capture any significant fragments of the clot, and the surface of the radially extended fiber element can provide an effective surface for pushing the clot. The fiber-based filter element can be further supported with struts and/or with a supplemental engagement structure that facilitates movement of the clot. A supplemental engagement structure can be integrally constructed with the fiber-based filter device or separately delivered over the wire supporting the filter device. A supplemental engagement structure may also provide for deployment of the fiber based structures to an extended filtering configuration. An aspiration catheter can be used to facilitate removal of the clot and the device while reducing the risk of losing significant fragments of the clot within the blood vessels.

In some embodiments of improved stroke directed embolectomy procedures described herein, the clot is first crossed. For example, the clot can be crossed directly with a filter device. In other embodiments, the clot can be crossed with a microcatheter, which then provides for the delivery of the filter device through the microcatheter. If desired, a guidewire can be first used to cross the clot where the guidewire has suitable flexibility for placement within a cerebral artery. A microcatheter can then be advanced over the guidewire and past the clot. Following removal of the guidewire, the lumen of the microcatheter provides a passage for the delivery of a fiber-based cerebral embolectomy device.

Following the delivery of the cerebral embolectomy device past the clot, the microcatheter may be withdrawn. After deployment of the cerebral embolectomy device, the device can be used to pull the clot from its resting point in a proximal direction. In some embodiments, the clot is pulled a significant distance such that the clot is out of the cerebral arteries and in an interior carotid artery. If the clot is pulled to the interior carotid artery, the clot may be pulled past one or more branches in the vasculature. The vessel diameter can increase significantly over the range in which the clot is pulled.

In additional or alternative embodiments, after the microcatheter is removed, an angioplasty balloon, stent delivery device, atherectomy device, or other mechanical treatment device for contributing to opening the vessel can be tracked to the clot over the guidewire. Such mechanical treatment devices are known in the art. The mechanical treatment device can be then used to mechanically engage the clot to disrupt the clot. The fiber-based filter device can be deployed downstream from the clot to trap any debris that may be generated from the clot. After use, the mechanical treatment device can be removed from the artery. Then, the clot and/or fragments thereof are removed using the fiber-based filter device along with appropriate suction. As with other embodiments, a supplemental engagement structure can also be used to facilitate removal of the clot and/or clot fragments.

In general, the filter element is designed to fill the vessel diameter to the vessel walls with the fiber matrix contacting or conforming to the wall of the vessel around the inner perimeter of the vessel. The filter element is generally delivered to the clot in a low profile configuration and transitioned to an extended configuration comprising a filtration matrix that can contact or conform to the vessel walls around the inner perimeter of the vessel. A fiber mat of the extended non-woven fibers forms a filtration matrix for blood to flow past the device. The properties of the filtration matrix can be adjusted as desired within a range of reasonable parameters. In some embodiments, the fiber mat is resilient so that the fiber mat continues to contact the vessel wall along the changing inner perimeters of a vessel while the clot is moved within the vessel toward a catheter used to remove the clot. At some point prior to removal of the clot from the patient, the clot is brought within a catheter for the remainder of the distance out from the body. The filter element or a portion thereof can be similarly brought into the catheter at its distal end to complete its removal from the patient. Aspiration can be supplied through the catheter to facilitate removal of the clot and fragments of the clot, which may or may not be associated with the filter element.

A supplemental engagement structure can be similarly delivered in a low profile configuration and extended after being placed at an appropriate position in the vessel. The engagement structure can be constructed from metal wire, such as a shape memory metal, or with higher gauge polymer filaments. Suitable shape memory metal includes, for example, cobalt alloys, such as Elgiloy®, a cobalt-chromium-nickel alloy, MP35N, a nickel-cobalt-chromium-molybdenum alloy, Nitinol®, a nickel-titanium alloy, and combinations thereof. The shape memory metals can be straightened for delivery such that they resume an extended configuration upon release within the vessel. The heavier gauge polymer filaments and metal wires generally are delivered in smaller number such that their bundle or configuration is thin enough for delivery through a microcatheter. The smaller number of polymer filaments or the metal wires may not form a reasonable filtration matrix and may or may not extend outward to the vessel wall to fill the vessel lumen, but the supplemental engagement structure can provide greater mechanical strength for moving the clot, while providing suitable flexibility for delivery into a cerebral artery. In some embodiments a combination of polymer filaments and metal wires are used. In general, throughout the description herein, the term filaments refers to fibers that has relatively thicker diameter than fibers used to form the three dimensional filtration matrix unless explicitly noted otherwise.

The use of a filter element can provide desirable properties with respect to clot removal. In particular, filters with a three dimensional filtration matrix can conform to the surface of the particle to spread the forces over the surface of the clot. The more uniform application of force may reduce the risk of wedging the clot in place, and may result in a higher success rate for being able to dislodge and the removal of the clot. Furthermore, if portions of the clot may break free from the main section of clot, the filter element can trap the fragments and facilitate removal of the clot while allow substantial amount of the flow to pass through. Thus, a three dimensional filtration matrix can provide an improved element for the displacement of the clot for removal. If a supplemental engagement structure is used, the fiber-based filter element provides additional support for moving the clot as well as a collection element for capturing fragments that may break off from clot during movement of the clot.

Embolic protection devices based on fibers can be effective at performing some embolectomy procedures. Embolectomy procedures, in general, using fiber-based embolic protection devices are described further in published U.S. patent application 2008/0172066 to Galdonik et al., entitled "Embolectomy Procedures With a Device Comprising a Polymer and Devices With Polymer Matrices and Supports," incorporated herein by reference. A fiber-based embolic protection device supplied by Lumen Biomedical, Inc. called FiberNet® has been approved for use in embolectomy procedures within peripheral blood vessels. However, delivery of devices into cerebral arteries provides challenges for fiber based devices even though the filter structure has a small lateral extent after deployment and the fibers themselves can be flexible. The devices described herein provide significant advances in the technology for the removal of clots from cerebral arteries.

The cerebral embolectomy device generally comprises a fiber-based component and a guide structure such as a very flexible wire, associated with the fiber based component. Upon delivery into the cerebral vessel, the fiber-based component or portions thereof can have a small radial profile so that the device maintains sufficient flexibility for tracking along the circuitous route into the cerebral artery. The fiber-based component or a portion thereof may or may not be secured to the flexible wire. If the fiber-based device is not secured to a flexible wire, the fiber-based device can slide over a flexible wire for placement, for example, until encountering a stop or the like on the flexible wire. In some embodiments, the fiber-based device can comprise a plurality of physically distinct components that are engaged together to form the filter structure. If there is a plurality of distinct fiber-based elements, one or more of the elements can slidably engage a flexible wire for placement in the patient. Similarly, a supplemental engagement structure can slidably deploy over the flexible wire or the structure can be integral with an element of the fiber-based device and the flexible wire.

The fibers in a fiber-based device component generally have at least one end secured to an attachment element. In some embodiments, a bundle of fibers are secured at an end at a common attachment element. The second end of the fibers may or may not be secured. If the second end of the bundle of fibers is not secured, the second ends of the fibers can flare out radially from the flexible wire to participate in the formation of the filtration matrix formed from a non-woven fiber mat. If the second end of the fibers in the bundle is secured, such as in a bundle to another attachment element, the drawing of the secured second ends of the fibers toward the secured first ends of the fiber flares the center of the fibers radially outward away from the guide structure to contribute to the formation of the three dimensional filtration matrix. The manipulation of the fiber-based element to transition the fibers is described further below. A plurality of fiber-based components may or may not have a common structure with respect to attachment of the fiber ends.

For delivery into a cerebral artery, it is desirable for the device overall to have a relatively small diameter to facilitate the navigation of tight curves. Thus, it may be desirable for a fiber bundle to comprise a modest number of fibers. To provide for desired diameters while providing a desired three-dimensional structure for the filtration matrix, it may be desirable to form the overall filtration matrix from a plurality of fiber bundles such that the combined bundles provide a desired total number of fibers in the overall deployed device. The plurality of fiber bundles can be supplied with a plurality of distinct fiber-based components with each component supplying at least one bundle of fibers and/or subdividing a longer length of fibers such that portions of a fiber deploy into a component of the filtration matrix as separate bundles of fibers. If there is a plurality of fiber elements, the fibers within the elements may or may not be the same as the fibers in each separate element. For example, a length of fiber arranged in a bundle around the flexible wire can be constrained with wrapped strip of polymer shrink wrap, such as a polyester, a band or the like at a position along the length of the fiber to divide the fibers of the bundle into groups so that the separate groups deploy separately. High strength medically approved heat shrink tubes are commercially available. The constrained portion can slide along a guide structure similar to an anchor such that the portion of the constrained fibers functions as a secured second end for one segment of the fibers while functioning as an secured first end for another segment of the fibers. Thus, in these embodiments, lengths of fiber, whether or not portions of the same physical fiber, compensate for reduced diameters of fiber bundles to form desired filtration matrices.

The fibers generally can have a stiffness that balances several factors. The fibers should be sufficiently flexible that the fibers fold into a fiber mat that forms a filtration matrix. The flexible fibers generally do not damage the vessel walls since they are flexible. Flexibility also facilitates movement of the device in a low profile configuration into the vessel. However, the fibers can have sufficient stiffness to provide for engagement and movement of the clot. The fibers can have a circular, elliptical or other reasonable cross-sectional shape. In some embodiments, surface capillary fibers can be used. The fibers in the same bundle may or may not be the same type of fibers. In some embodiments, it may be advantageous to combine fibers of different mechanical and filtration properties into the same bundle to achieve desired clot retention and filtration effect.

As noted above, the fiber-based device can have a narrow profile configuration for placement into the cerebral artery and an extended configuration that forms a filtration matrix. In general, with respect to the transition of the fiber-based device between configurations, the fiber-based device can be self-actuating and/or actuated with a push catheter or the like. In the self-actuating version of the device, the fibers can be formed with a shape memory. Thus, once the fibers are released, such as from a microcatheter, the fibers resume a natural configuration extending radially from a flexible delivery wire to form the filtration matrix. Fiber bundles that are actuated can be of particular interest for some embodiments since the individual fibers can be thin and flexible while the bundle can be deployed into a desirable configuration with a suitable actuation device. Additionally or alternatively, struts can accompany the fibers, in which the struts deform upon release, such that the deformed struts tend to extend the fibers outward radially.

Struts or other support structures can also add mechanical stability to the filtration matrix to facilitate the use of the filtration matrix to stabilize and/or push the clot. In some embodiments, the struts are designed to avoid contacting the vessel walls such that the struts do not injure the vessel walls. Support structures can be self-extending to form a more open support structure that supports a fiber-based matrix, although in other embodiments, the support structure is also actuated to assume a deployed configuration, such as using a common actuation tool with the fiber-based device. Suitable memory polymers are described further in U.S. Pat. No. 6,160,084 to Langer et al., entitled "Biodegradable Shape Memory Polymers," incorporated herein by reference. Other suitable memory polymers include, for example, hydrophilic polymer fibers, including, for example, polyester fibers. These polymer fibers can be gently heated to introduce desired curvatures, and then mechanically straightened for placement in the vessel until released at the point of use. Suitable spring metals that can be used for self actuating struts include, for example, cobalt alloys, such as Elgiloy®, a cobalt-chromium-nickel alloy, MP35N, a nickel-cobalt-chromium-molybdenum alloy, and Nitinol®, a nickel-titanium alloy.

An actuation tool, such as a push catheter or the like, can be used to actuate the fibers to an extended configuration with a filtration matrix through advancement over the flexible wire supporting the fiber-based elements of the clot engagement structure. If the fiber-based device is self-extending, the actuation tool can further be used to facilitate full extension or assumption of a particularly desired configuration. In some embodiments, an actuation tool is used to induce the transition of the fibers to an extended configuration forming a fiber mat as a filtration matrix. For example, the actuation tool can engage an attachment element with a plurality of attached fiber ends to move the attachment element along a delivery wire to extend radially outward the center of the fibers. In additional or alternative embodiments, the actuation tool, optionally with an extending engagement tool, can interface with free ends of a fiber bundle to flare the ends of the fibers into an extended configuration. If there is a plurality of fiber-based devices laterally extended along a delivery wire, a push catheter can be used to extend all of the fiber-based devices into extended configurations. An actuation tool may also function as a support structure for the fiber-based element following deployment of the element. In additional or alternative embodiments, the actuation tool may also actuate deployment of a support structure separately or along with the deployment of the fiber-based element.

The filter matrix, optionally with a supplemental support or engagement structure, can stabilize and/or move the clot in a proximal direction within the vessel, and the clot can be removed through a catheter. For softer clots, aspiration can be used to withdraw the clot into the catheter without further intervention. For harder or more calcified clots, the clot can be fragmented using force between the catheter and the filter element to break up the clot into smaller pieces that can be removed into the catheter. In some embodiments, the clot can be wedged between a small catheter and the filter element for movement in a proximal direction to deliver the clot to a larger diameter catheter that can move easily to remove the clot from the blood vessel.

In some embodiments, the filter element can be positioned adjacent or contacting the clot as the clot is aspirated from the blood vessel. In additional or alternative embodiments, the filter element can be placed contacting the distal side of the clot as a catheter is contacted with the proximal side of the clot to fragment the clot for removal from the vessel. In these embodiments, the catheter can have a small diameter and a high degree of flexibility such that the distal end of the catheter can be brought optionally into a cerebral artery in the vicinity of the clot. The filter element can be used to displace the clot in a proximal direction, i.e., upstream within the vasculature toward a catheter within the cerebral artery. The nature of the filter with a three dimensional filtration matrix provides for effective movement of the clot with good control of the procedure and a low risk of re-embolization of clot fragments.

To perform the procedures in a cerebral artery, a guide catheter is generally initially placed in an interior carotid artery. The devices for the procedure in the cerebral artery can be then delivered from the guide catheter. The guide catheter can be supplied with a partially or fully occluding element, such as a balloon, that can temporarily block or reduce flow into the cerebral arteries to facilitate removal of the clot. Catheters with partially occluding structures are described, for example, in published U.S. patent application 2007/0060908A to Webster et al., entitled "Thrombectomy Catheter," incorporated herein by reference.

The procedure is generally guided by appropriate visualization techniques. For example, the initial location of the clot can be identified, for example, with a CAT scan, with or without contrast dye, to identify the location of treatment. During the procedure, the placement of components of the devices generally is guided by appropriate imaging techniques, such as real time x-ray imaging. To facilitate this process, the devices can comprise radiopaque components to facilitate this process. Suitable radiopaque components include, for example, marker bands, radiopaque fibers and other radiopaque components.

In some embodiments, it can be desirable to pull the clot out from the cerebral arteries into an interior carotid artery. In the interior carotid artery, the clot can be aspirated with a guide catheter or other larger lumen catheter. A circuitous pathway connects the interior carotid arteries with the cerebral artery system. Due to this highly curved transition between the vessels, there are significantly fewer structural limitations with respect to a catheter in a carotid artery compared with a catheter that is delivered into a cerebral artery. In particular, a catheter for delivery into a cerebral artery necessarily has a smaller lumen and is more flexible. The features that make a catheter suitable for placement into the cerebral artery make it difficult to apply a desired degree aspiration, such as with respect to volume and flow rate, into the catheter for the removal of the clot, which can be combined with removal of the filter element.

Therefore, it can be desirable to pull the clot into the carotid artery for removal into a catheter. However, this movement of the clot can provide significant design constraints on the filter element. In particular, the fiber-based clot engagement element generally is designed to conform to the vessel walls around inner perimeter of the vessel such that the element functions essentially as a filter. If the clot engagement element along with a clot is moved a significant distance upstream, vessel branches can be passed and generally the vessel diameter increases, and the increase can be significant if the clot is moved some distance. For example, it is possible for the vessel diameter to increase by as much as a factor of two or more. Since the vessel diameter can change by more than a factor of two, the fiber matrix can be designed to have the ability to have significant expansion to adapt to changes in the vessel diameter. The filter element can be designed to maintain contact with the vessel wall as the vessel diameter around the filter element increases due to the upstream movement of the filter. If the filter maintains contact with the vessel wall, the filter element can reduce or eliminate emboli from flow downstream from the clot until the clot is removed.

The filter or fiber-based clot engagement element is intended for placement downstream from the clot. To accomplish this objective, the filter element generally is associated with a very flexible wire that can navigate the circuitous vascular pathway from an interior carotid artery to the location of the clot in the cerebral artery. Since several sharp turns in the blood vessels are located at the end of the cerebral arteries adjacent to the interior carotid arteries, sharp turns are necessarily encountered for placement of a device into the cerebral arteries from an interior carotid artery, although additional turns characterize the cerebral artery system. Association of the clot engagement, i.e. filter, element with a corresponding delivery wire should not destroy the ability of the wire to navigate the turns, although delivery of the clot engagement element onto the wire after delivery of the wire can indirectly address these concerns.

Generally, the clot engagement element, i.e., filter elements, comprise fibers that deploy into a fiber mat, which can form a three dimensional filtration matrix. The filter element is associated with a flexible delivery wire. The filter element or portion thereof may or may not be fixed to the delivery wire. In some embodiments, the filter element or portions thereof can be tracked over the delivery wire after placement of the delivery wire. If appropriate, the delivery wire can comprise a stop element to engage a fiber based element portion tracked over the delivery wire. In additional or alternative embodiments, the filter element or a portion thereof can be attached to the delivery wire such that it is introduced into the patient with the delivery wire. In some embodiments, a portion of the fiber-based filter element is attached to the delivery wire while other portions are delivered over the delivery wire. Regardless of whether or not the fiber-based filter element comprises a portion connected with the delivery wire, the filter element can optionally comprises physically distinct elements that can be assembled into the filter element for use.

In some embodiments, the clot removal procedure comprises the delivery of a guide catheter into an interior carotid artery. Then, a guide wire or the like can be delivered into a cerebral artery with the distal end placed past a clot within the cerebral artery. A microcatheter can be delivered over the guidewire with its distal end past the clot, and the guidewire can then be removed. A flexible wire that supports the fiber-based clot engagement element can be delivered through the microcatheter. If appropriate, components of the fiber-based clot engagement element and/or a support element can be delivered over the flexible wire. A deployment tool can be delivered to facilitate transition of fibers to a deployed configuration extending outward relative to the flexible wire to contact vessel walls, and the delivery of the deployment tool can be performed after removing the microcatheter. Once the fiber-based element is fully assembled and deployed along with any support structures, the clot can be engaged for removal. The clot can be brought to an aspiration catheter, which can be positioned within a cerebral artery or an internal carotid artery. In some embodiments, the guide catheter within the interior carotid artery can be used as an aspiration catheter. With the clot engagement structure or element deployed, an auxiliary treatment structure, such as an atherectomy device, a stent, an angioplasty balloon or the like can be deployed prior to translation of the clot engagement structure or element in a proximal direction.

Other devices have been designed with the objective of removing clots from vessels. In general, these devices are designed to grip the clot or fragments thereof to effectuate its removal. For example, spiral shaped devices for gripping clots are described in U.S. Pat. No. 7,534,252 to Sepetka et al., entitled "Systems, Methods and Devices for Removing Obstructions from a Blood Vessel," incorporated herein by reference. A device designed for gripping clots from a proximal approach is described further in published PCT application WO 2006/031410A to Bose et al., entitled "System and Method for Treating Ischemic Stroke," incorporated herein by reference. In contrast with these devices the present devices are intended to stabilize and pull the clot without necessarily gripping the clot. Also, the fiber-based devices described herein can effectively provide a filtration function to reduce or eliminate re-embolization.

Fiber bristle devices for removing clots are described in published U.S. patent application 2009/0306702 to Miloslavski et al., entitled "Device for the Removal of Thrombus," incorporated herein by reference. These devices have a brush style design intended to capture and/or fragment the clot while gripping fragments. In contrast, the present devices are intended to form a filtration matrix with a relatively small lateral extent that provides for pushing the clot for removal with a catheter. The filtration matrix may additionally capture and retain any debris or break off from the clot during the removal process. The fibers of the devices herein are incorporated into a significantly different structure to provide correspondingly different functionality. In particular, the fibers of the element generally are very thin such that a mat of fibers can be formed with appropriate filtering ability without damaging the vessel walls and in some embodiments having the ability to conform to changing diameters of the vessel walls as the element is moved within the vasculature. The combination of a fiber-based element that forms a fiber mat with a support element can be particularly effective based on the combined features of the components.

Structural Elements of the Embolectomy Devices and Methods of Making

The embolectomy devices generally comprise a flexible wire and a fiber-based clot engagement structure or element that engages the flexible wire. The fiber-based elements generally comprise a bundle of fibers, generally in a non-self extending structure, in which the fibers may be fixed at one or both ends to an anchor or the like. The devices can further comprise a support structure and/or an actuation tool that also engage the flexible wire. A support structure may or may not also function as an actuation tool. The components that engage the flexible wire may slide over the flexible wire or are connected fixedly to the flexible wire. One or more catheters can be used to facilitate the procedure, such as a guide catheter, a microcatheter and/or an aspiration catheter, although the guide catheter can also be configured as an aspiration catheter. The proximal end of the device, introducers, hemostatic valves and the like, such as those elements known in the art, can be placed to provide for introduction of elements into the patient's blood vessel, and various fittings, such as Luer lock fittings and the like, can be used for the delivery of the various components outside the patient by guiding the components into the patient's blood vessels.

Referring to FIG. 1, two embodiments of the fiber bundle in different configurations are illustrated. FIG. 1(a) is a side perspective view of a fiber cartridge 100 with a bundle of fibers 102 having one end fixed with a fiber attachment element 104 while the other end of the fibers remain un-constrained. The fibers in the bundle generally align along a guide wire 108 in a narrow profile configuration. FIG. 1(b) shows a fiber cartridge 200 with a bundle of fibers 202 having both ends fixed with fiber attachment element 204 and 206, respectively. The middle portion of the fibers is not secured or constrained. The fibers in the bundle 200 generally align a guide wire 208 in a narrow profile configuration. Both fiber bundles 100, 200 can be designed for fixed attachment to the wire 108 or 208 through fiber attachment elements 104 or 204, respectively. In some embodiments, the fiber attachment elements have a slide that can translate over the delivery wire or an anchor that is secured at a fixed position of the delivery wire. The wire 108 and 208 can be the delivery wire or can have a lumen to slide over a separate delivery wire. The un-constrained portion of the fibers can flare radially outward to an extended deployed configuration. Referring to FIG. 1(c), a side perspective view of the fiber cartridge 100 of FIG. 1(a) is shown in an extended deployed configuration. Referring to FIG. 1(d), a side perspective view of the fiber cartridge 200 of FIG. 1(d) is shown in an extended deployed configuration. The unconstrained end or portion of the fibers flares outward to form a three dimensional filtration matrix that is capable of retain clot while trapping break-offs from the clot.

The fibers of the fiber bundle can be approximately uniformly fixed around a central axis approximately at the center of the attachment element. Also, the attachment element generally has a central lumen roughly aligned with the central axis for sliding over the flexible delivery wire or is attached fixedly to the flexible delivery wire roughly at the position of the central axis. The approximate cylindrical symmetry of the bundle around the delivery wire facilitates the deployment of the fiber bundle into a filter matrix that has a desirable configuration across the blood vessel upon deployment. The fibers can be selected to have desired mechanical properties in the vessel. In general, the fibers should be flexible so that the fibers can be delivered into the vessel and such that the fibers do not injure the vessel wall. Generally, the fibers are formed from polymers, such as organic polymers. Suitable polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof. Fibers can be formed from a radiopaque material, as described in published U.S. patent application 2007/0172526A to Galdonik et al., entitled "Radiopaque Fibers and Filtration Matrices," incorporated herein by reference.

The fibers can have a suitable cross sectional shape to provide desired mechanical properties. In some embodiments, the fibers can have a circular cross section, oval cross section or other convenient shape. In some embodiments, surface capillary fibers can be used, which have one or more surface capillaries extending along the length of the fiber. The use of surface capillary fibers for three dimensional filtration matrices for embolic protection devices is described further in published U.S patent application 2005/0209631A to Galdonik et al., entitled "Steerable Device Having a Corewire Within a Tube and Combination With a Functional Medical Component," incorporated herein by reference.

A particular device can comprise one or more types of fibers. In some embodiment, the same bundle of fibers can comprise one or more types of fibers to provide desired mechanical and filtration properties. The thickness of the fibers can be selected appropriately for the particular use of the fiber. Fiber thickness can be measures in several ways. The radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude.

Also, in the fiber field, a pragmatic way has been developed to characterize fiber thickness without the need to resort to magnification of the fibers. Thus, fiber thickness can be measured in units of denier. Deniers correspond to the number of grains per 9,000 meters of yarn with a larger value corresponding to a thicker fiber. In some embodiments, suitable fibers have diameters from 1 micron to about 75 microns, in further embodiments from about 2.5 microns to about 50 microns, and in additional embodiments from about 5 microns to about 40 microns. As measured in denier, suitable fibers can have sizes ranging from about 0.02 denier to about 50 denier in size, in additional embodiments from about 0.05 denier to about 30 denier, in some embodiments from about 0.1 denier to about 20 denier, in other embodiments from about 0.2 denier to about 15 denier and in further embodiments from about 0.4 denier to about 10 denier. As noted above, supplemental engagement or support structures can be formed from thicker filaments, which are generally included in smaller numbers to provide added support to the fiber-based clot engagement structures. For filaments included in a supplemental support structure, the filaments generally have a diameter from about 15 microns to about 300 microns (0.3 mm, 0.012 inches), in further embodiments from about 20 microns to about 275 microns and in other embodiments from about 250 microns. The number of fibers can be selected based on the diameters with the constraint of the inner diameter of a delivery catheter, such as a microcatheter. For a supplemental support structure, the structure can comprise from about 4 to about 25 polymer filaments. For the fiber based filter structure, a bundle of fibers generally comprises from about 25 to about 500 fibers, in further embodiments from about 30 to about 400 fibers and in additional embodiments from about 35 to about 300 fibers. A range of biocompatible polymers have been approved for use in a devices placed into patients, such as polyesters. A person of ordinary skill in the art will recognize that additional ranges of fiber thickness in diameter measurements or in denier and fiber numbers are contemplated and are within the present disclosure.

The lengths of the fibers should be selected such that the deployed fibers fill the vessel lumen. Thus, if the fibers are bent in the deployed configuration, the fibers should have lengths greater than a factor of 2 larger than the vessel radius. The devices can be supplied with different sizes available for selected deployment based on the size of a particular target vessel. If the devices are designed for movement of a clot to the carotid artery, the size of the carotid artery can be used to select the device size without reference to the size of the vessel where the clot is initially located. In some embodiments relating to the use of a plurality of fibers to expand within the lumen of a patient's vessel, it is generally appropriate to use fibers that have a length from about 2.2 to about 15 times the vessel radius, in some embodiments from about 2.4 to about 12 times the vessel radius and in further embodiments from about 2.6 to about 8 times the vessel radius. In particular, if the fiber-based filter element is used to drag the clot into the carotid artery, the vessel diameter around the filter element can change, for example, from roughly 1.5 to 2 mm in diameter to about 5.5 to 6 mm in diameter. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure.

For spring metal elements, either struts or elements for a supplemental engagement structure, the spring metal elements generally have a circumference from about 0.001 inches (24 microns) to about 0.05 inches (1200 microns), in further embodiments from about 0.002 inches (48 microns) to about 0.03 inches (7200 microns) and in other embodiments from about 0.003 inches (72 microns) to about 0.02 inches (480 microns). In general, the supplemental engagement structure comprises from about 2 to about 10 wires or other shaped elements of spring metal. A person of ordinary skill in the art will recognize that additional ranges of diameters and number of wires within the explicit ranges above are contemplated and are within the present disclosure. The metal elements generally can have any reasonable cross sectional shape consistent with the element design, such as round or ribbon shaped. The appropriate length of the metal element depends on the specific design and should be consistent with the deployed shape within the vessel.

In general, catheters can be formed from metal, polymers and combinations thereof. For example, some catheters can be formed from polymer tubes with embedded metal reinforcement. Flexible wires and other metal elements can be formed from stainless steel, titanium, spring metals, combinations thereof or the like.

Figure 2:
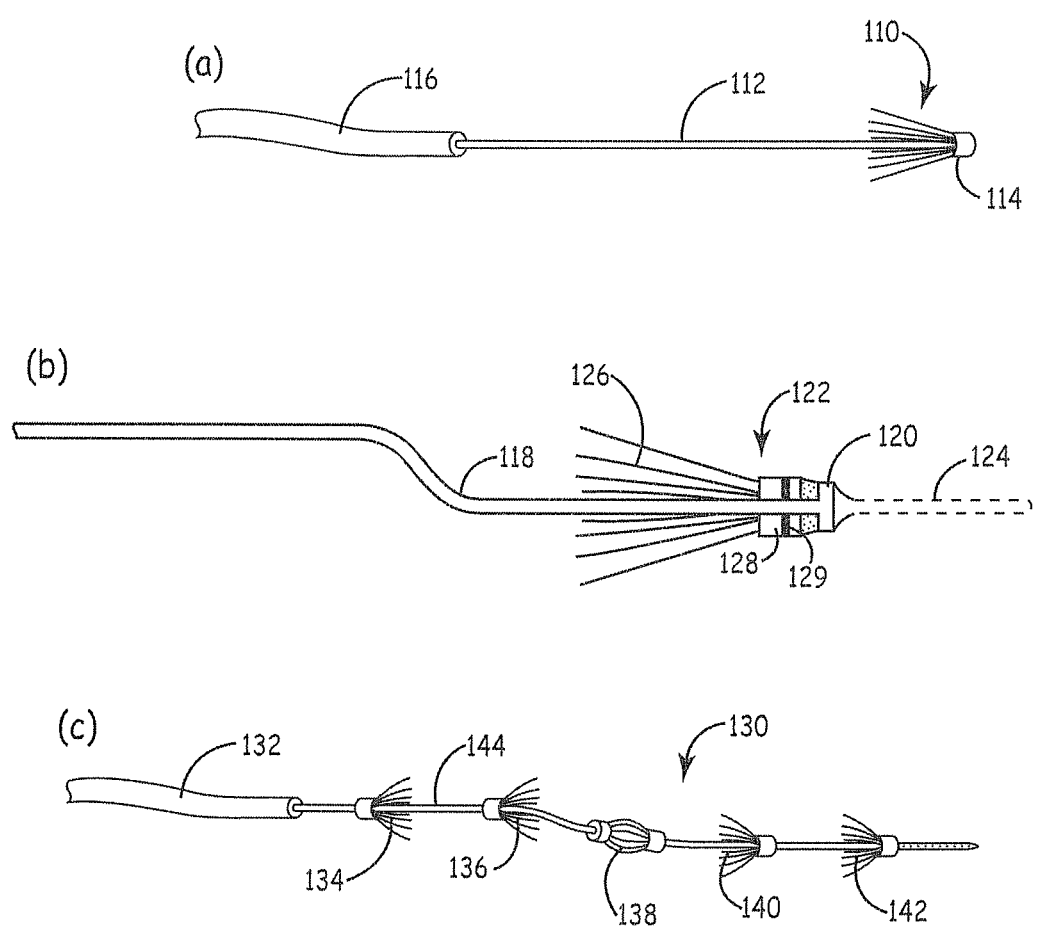
FIG. 2(a) is a fragmentary side perspective view of a filter element fixed to a delivery wire protruding outside a microcatheter.
FIG. 2(b) is a fragmentary side view of a delivery wire with a stop and a slidable filter element engaging the stop.
FIG. 2(c) is a fragmentary side view of a plurality of filter cartridge bundles in a combination advanced out of a microcatheter along a flexible wire.

Referring to FIG. 2, embodiments of microcatheter with filter elements are illustrated. FIG. 2(a) is a fragmentary side perspective view of a filter element comprising a fiber bundle 110 with a single bound end 114 fixed to a delivery wire 112 protruding distally outside a microcatheter 116. FIG. 2(b) is a fragmentary side view of an embodiment with a delivery wire 118 that has a stop 120 and a filter element 122 that slides over the delivery wire until it hits the stop. The rigid stop 120 at or near the distal end portion of the device generally has a diameter larger than the body of the delivery wire 118. The delivery wire 118 may additionally have an optional coil tip 124 to facilitate the maneuver of the delivery wire inside a blood vessel. In some embodiments, the filter element 122 comprises a bundle of fibers 126 that can be attached to a fiber attachment element 128 with an adhesive, a band or the like and/or melted polymer from heat bonding the fibers of the bundle.

The ends of the fibers can be secured in a roughly parallel orientation relative to the flexible delivery wire and approximately uniformly distributed around the circumference of the delivery wire. The orientation of the fixed ends of the wire is consistent with a low profile delivery configuration of the fibers aligned approximately along the axis of the delivery wire. If desired, a radiopaque band 129 can be secured at the fiber attachment element 128. FIG. 2(c) shows another embodiment of a filter element 130 advanced out of distal end of a microcatheter 132. The filter element comprises a combination of filter cartridge bundles 134, 136, 138, 140, and 142 distributed along the distal portion of the delivery wire 144. The number, the orientation, and the composition of the fiber cartridge bundle can be varied to suite a variety of needs. In the embodiment shown in FIG. 2(c) for example, fiber bundles 134 and 136 assumes an opposite orientation compared to the fiber bundles 140 and 142, while fiber bundle 138 has both ends of the fibers constrained. The fibers bundles shown in FIG. 2(c) once deployed may provide complementary mechanical and filtration properties to result in improved performance in clot removal process. In general, the device can comprise one fiber bundle, two fiber bundles, three fiber bundles, four fiber bundles, five fiber bundles, six fiber bundles or more than six fiber bundles. In some embodiments, at least some of the fibers bundles are non-woven. The fiber bundles can be made out of same or different materials, having the same or different constructions, as well as the same or different sizes in terms of number of fibers used, the length and thickness of the fibers used. The fiber bundles can assume any of the structure described herein.

Figure 3:
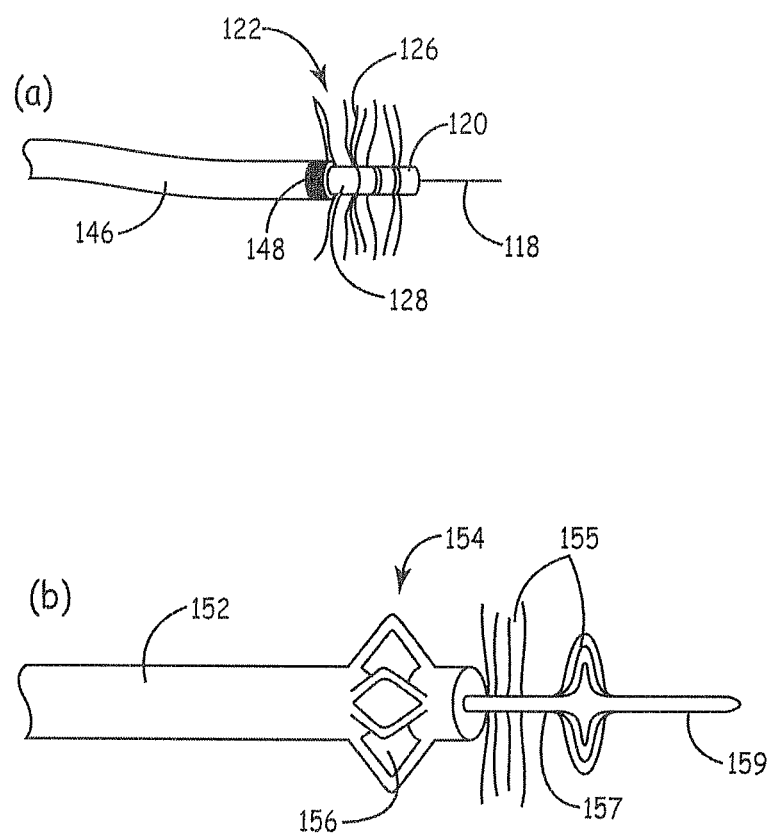
FIG. 3(a) is a fragmentary side view of a deployed fiber-based filter element that is maintained in the deployed configuration due to the interaction of the fiber bundle with a microcatheter.
FIG. 3(b) is a fragmentary side view of a push catheter with a slotted distal end helps to deploy a filter element extended out of the push catheter.

Referring to FIG. 3, embodiments of interaction between filter element and push and/or micro catheter are shown. FIG. 3(a) shows the filter element 122 of FIG. 2(b) fully deployed by its interaction with a microcatheter 146. Specifically, the filter element 122 comprises a plurality of fibers 126 having one end of the fibers fixed on a fiber attachment element 128 that is delivered on a guidewire 118. After the filter element 122 is advanced out of the microcatheter 146, the non-bound or non-fixed end of the fibers flares slightly such that when the fiber element is pulled against the microcatheter, the fibers 126 becomes fully extended to a fully deployed configuration. If desired, a radiopaque band 148 can be secured at the distal portion of the microcatheter 146 to facilitate the delivery and deployment of the filter element and the microcatheter.

An optional push catheter may also be used. FIG. 3(b) shows an embodiment of the push catheter 152 having an extendable element or section 154 used to deploy a filter element 155. The filter element is delivered on a guidewire 157, which has an optional tip section 159 that provide additional navigation during the delivery. The expandable element 154 can be formed, for example, from a slotted tube 156 or separate micro-filaments fused to the catheter, although other extendable structures can be similarly used. The expandable element or section 154 can have a low profile configuration until push catheter 152 engages fiber-based element 155 such that the force against the fiber-based element extends the extendable element 154. A push catheter can optionally be used as a supplemental engagement structure such that the push catheter and fiber-based filter element are used together to remove the clot. The push catheter can serve a dual purpose of extending the fibers and facilitating the movement of the clot.

Figure 4:
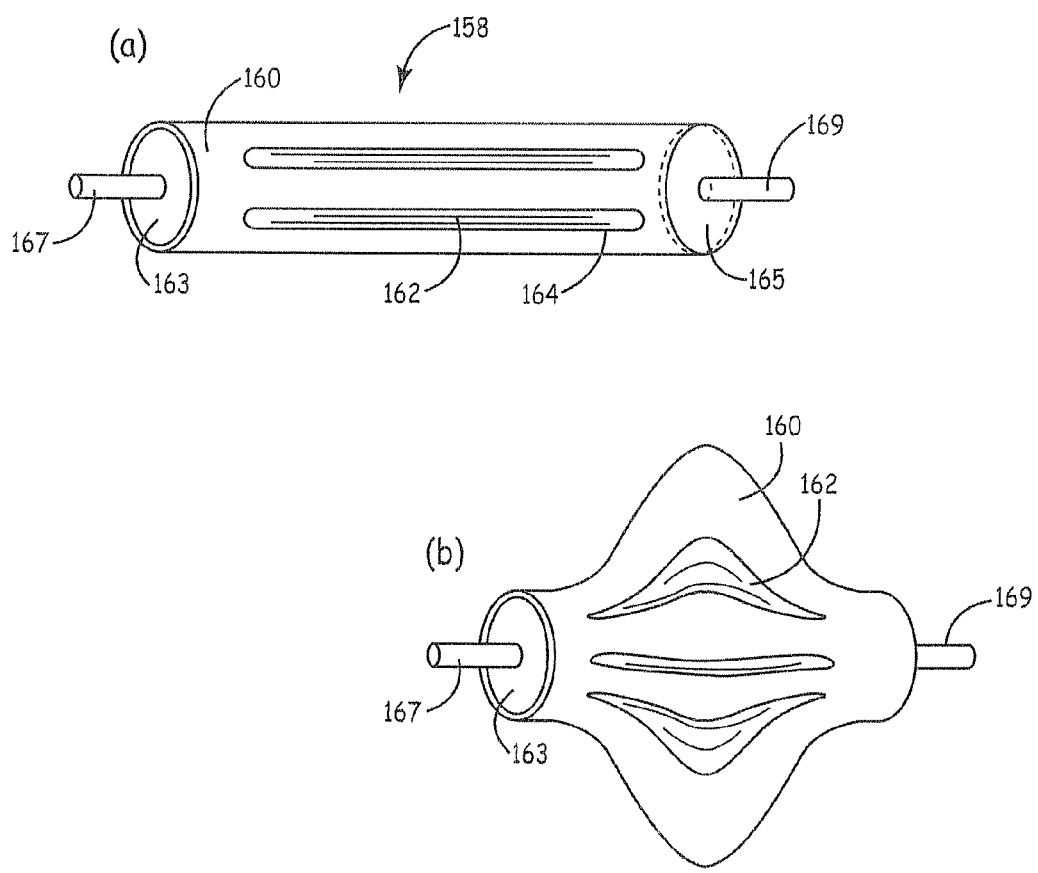
FIG. 4(a) is a perspective side view of a clot engagement element with a fiber bundle covered with an exterior slotted heat shrink jacket assembled in a cartridge that can slide over a flexible wire for delivery to a treatment location.
FIG. 4(b) is a perspective side view of the device of FIG. 4(a) in a deployed configuration.

Referring to FIG. 4, an embodiment of a fiber-based filter element 158 with a heat shrink sheet 160 combined with fibers 162 is illustrated in a low profile configuration and in an extended configuration. FIG. 4(a) shows a thin wall of heat shrink polymer jacket 160 on the exterior of a fiber bundle 162, in which the polymer jacket 160 has slits 164 such that the polymer jacket can assume the extended configuration. While a heat shrink polymer jacket can be convenient, other polymer jacket materials can be used and appropriately assembled, as desired. The fibers are fixed on one end to a first attachment element 163 and on the second end to a second attachment element 165. First attachment element 163 and second attachment element 165 are respectively associated with tubes 167 and 169 that have an inner diameter suitable for sliding over a flexible wire associated with delivery of the device past the clot. FIG. 4(b) shows the outer heat shrink jacket covers the fiber bundle in a deployed or extended configuration. This fiber-based element is deployed in a similar way as other fiber-based elements. The jacketed fiber-based elements of FIG. 4 can be used alone or in combination with other fiber-based element which may or may not have polymer jackets.

Figure 5:
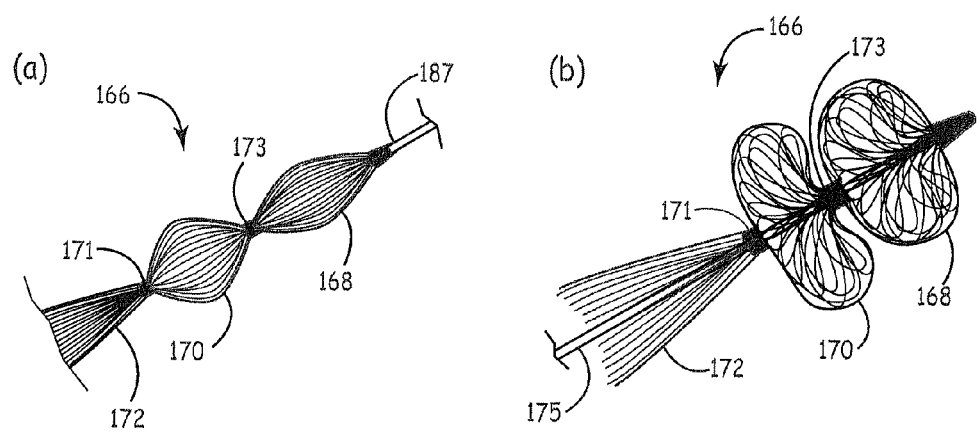
FIG. 5(a) is a photograph of a filter element comprising multiple fiber cartridges covered with heat shrink jacket in a narrow profile delivery configuration.
FIG. 5(b) is a photograph of the device of FIG. 5(a) in a deployed configuration.

Referring to FIG. 5, various views and configurations are shown of an embodiment of a filter element 166 comprising multiple fiber cartridges 168, 170, 172 with fiber tail formed from longer fibers and PET heat shrink jacket or structure support. Small sections of heat shrink wrap, which can be optionally replaced or supplemented with bands 171 and 173, such as radiopaque bands, metal bands, polymer bands or the like, effectively constrain and therefore divide long fibers into sections that separately deploy as fiber mats as a filtration matrix such that three distinct fiber mats 168, 170, and 172 are combined within the filtration matrix. The band 173 functions as a secured second end for fiber cartridge 168 while functioning as a secured first end for fiber cartridge 170. The band 171 functions as a secured second end for fiber cartridge 170 while functioning as a secured first end for fiber cartridge 172. The second end of the fiber cartridge 172 remains unconstrained. In some embodiments, the bands 171 and 173 can slide along the guide wire 175 similar to an anchor. An optional distal coil 187 can be integrated to the distal end of the guide wire 175 to facilitate the delivery of the device into a desired location inside a vessel. The overall lengths of fiber could compensate for reduced diameters of fiber bundles to form desired filtration matrices.

FIG. 5(a) is a side view of the filter element in a delivery or narrow profile configuration. FIG. 5(b) is a side view of the filter element of FIG. 5(a) in a deployed or extended configuration. In some embodiments, the bundle of the fibers is non-woven. Thus, in the embodiment of FIG. 5, multiple fiber-based elements are effectively formed from long fibers that are subdivided to form the individual fiber-based elements. The fiber-based element of FIG. 5 can be used in combination with additional fiber-based elements that are slide over the flexible wire. While FIG. 5 is directed to long fibers divided into three elements, long fibers can be similarly divided as desired into two elements, four elements, five elements or more than five elements.

Figure 6:
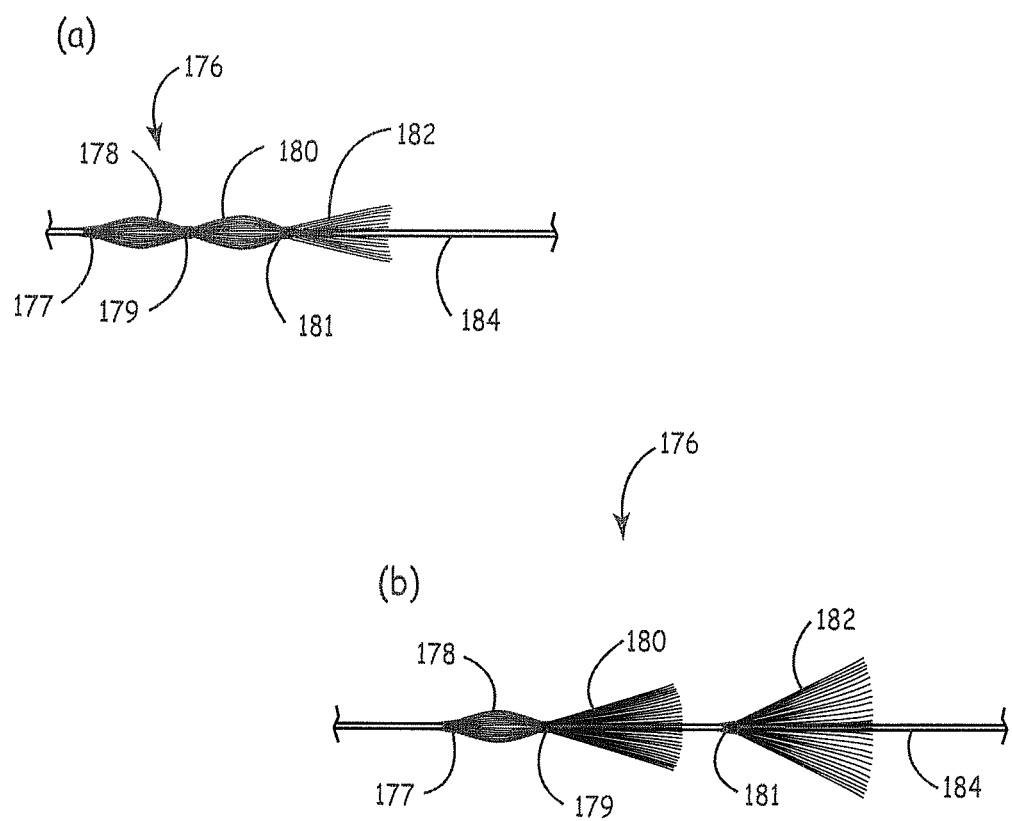
FIG. 6(a) is a fragmentary side view of a filter element comprising multiple free ended fiber cartridges with a fiber tail that slide along the delivery wire in a narrow profile delivery configuration.
FIG. 6(b) is a fragmentary side view of the device of FIG. 6(a) in a partially deployed or extended configuration.
Figure 7:
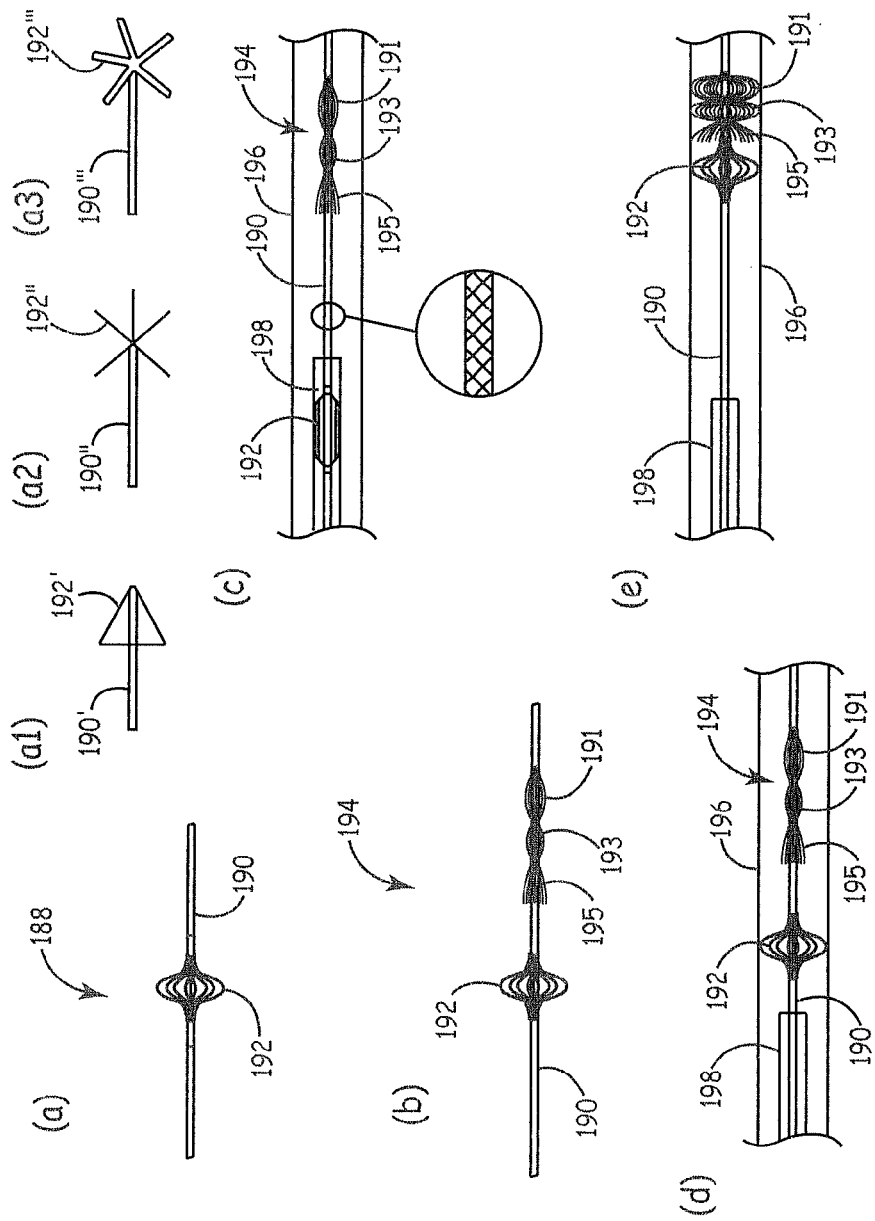
FIGS. 7(a1)-(a3) are schematic diagrams of various version of the push catheter with different deployment tools.

Referring to FIG. 6, various configurations are shown of a filter element 176 comprising multiple free ended fiber cartridges 178, 180, 182 with a fiber tail that slide along a delivery wire 184. FIG. 6(a) is a side view of the filter element 176 in a delivery or narrow profile configuration. Fiber cartridge 178 is secured at one end with a fiber attachment element 177, fiber cartridge 180 is secured at one end with a fiber attachment element 179, and fiber cartridge 182 is secured at one end with a fiber attachment element 181. The free end of the fiber cartridge 178 can be temporarily constrained by the fiber attachment element 179, the free end of the fiber cartridge 180 can be temporarily constrained by the fiber attachment element 181, and the free end of the fiber cartridge 182 can remain unconstrained. FIG. 6(b) is a side view of the filter element 176 in a partially deployed or extended configuration where cartridge 182 slides along delivery wire 184 in an extended configuration. The free end of the fiber cartridge 180 is freed from the constraints of fiber attachment element 181 and is in a partially deployed configuration. The free end of the fiber cartridge 178 is constrained by fiber attachment element 179 and therefore is still in an un-deployed configuration. Referring to FIG. 7, deployment tools and application of a deployment tool is shown. FIG. 7(a) is a photograph of a push catheter 190 with a polymer filament cartridge 192 as the deployment tool 188 in an expanded configuration. The deployment tool can engage fibers of a filter element to extend the fibers to an extended configuration. FIG. 7(b) is a photograph of the push catheter 190 with the expandable element 192 in a reduced diameter delivery configuration in combination with a filter element 194. Push catheter 190 can be tubular, such as a metal, polymer or composite tube, an open woven structure as shown in the alternative embodiment in the insert of FIG. 7(c) since the push catheter does not hold fluid, or other appropriate structure that allows for pushing the deployment tool into position. The filter element comprises three filter cartridges 191, 193, and 195 that can be separate such as the embodiment shown in FIG. 6 or connected such as the embodiment shown in FIG. 5. FIG. 7(c) is a diagram of the device of FIG. 7(b) showing the filter element 194 inside a vessel 196 while the filament cartridge 192 in a reduced diameter delivery configuration inside a microcatheter 198 with the filter element 194 advanced distal to the filament cartridge 192. FIG. 7(d) is a diagram showing the filament cartridge 192 advanced outside the microcatheter 198 by the push catheter 190 and deployed into the extended configuration. FIG. 7(e) is a diagram showing the filament cartridge 192 advanced further to push the filter cartridges 191, 193, and 195 into a fully deployed configuration. The fully deployed filter cartridges have extended configurations that push against the wall of the vessel 196.

In some embodiments, the filament cartridge is self-extendable. FIGS. 7(a1)-(a3) are additional embodiments of the deployment tools. Specifically, FIG. 7(a1) is a schematic diagram of a push catheter 190' with triangular shaped filament cartridge 192' as the deployment tool in an expanded configuration. FIG. 7(a2) is a schematic diagram of a push catheter 190" with star shaped filament cartridge 192" as the deployment tool in an expanded configuration. FIG. 7(a3) is a schematic diagram of a push catheter 190''' with star shaped filament cartridge 192''' as the deployment tool in an expanded configuration. The star shaped filament cartridge 192''' can have padding to make the filaments thicker. The deployment tools can be formed from shape memory metals or suitable thicker polymer fibers.

Figure 8:
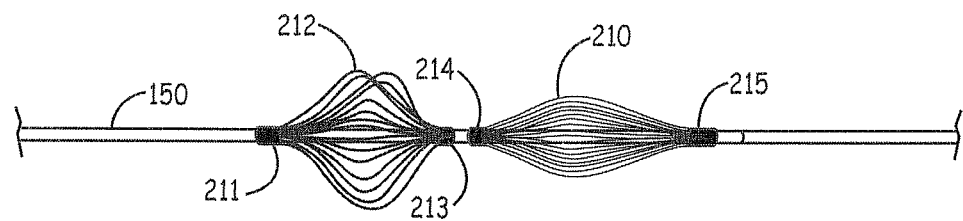
FIG. 8 is a fragmentary side view of a filter element coupled with a filament supplemental engagement structure.

Referring to FIG. 8, a side view of a device is shown. The device comprises a filter element 210 with a polymeric filaments supplemental engagement structure 212, comprising a plurality of polymeric filaments with both ends of the filaments secured by filament support structures 211 and 213. The filament support structures 211 and 213 can be fixed or slidable on the delivery wire 150. The filter element 210 comprises a bundle of fibers with both ends of the fibers secured by fiber attachment elements 214 and 215. The fiber attachment elements 214 and 215 can be fixed or slidable on the delivery wire 150. The filter element 210 and the polymeric filament supplemental engagement structure 212 may or may not be integrally constructed to be connected to each other. The supplemental engagement structure 212 is combined with the filter element 210 to provide support for the filter element so the combination can retain clot while effectively trap emboli by conforming to the inner perimeter of the vessel during the entire clot removal process. The filter element can then engage the clot as well as to provide the ability to capture any fragments of the clot that separates from the clot. In general, the filaments of the supplemental engagement structure are significantly thicker than the fibers of the filter element. The filaments may be self-extendable while the bundle of fibers is deployed into an extended configuration with appropriate actuation. The device may be contained in a microcatheter in a reduced diameter delivery configuration for placement within a vessel. Once the microcatheter is released, the filaments expand into an extended deployment configuration as shown. The filter element maybe independently deployed using a pushing element.

Figure 9:
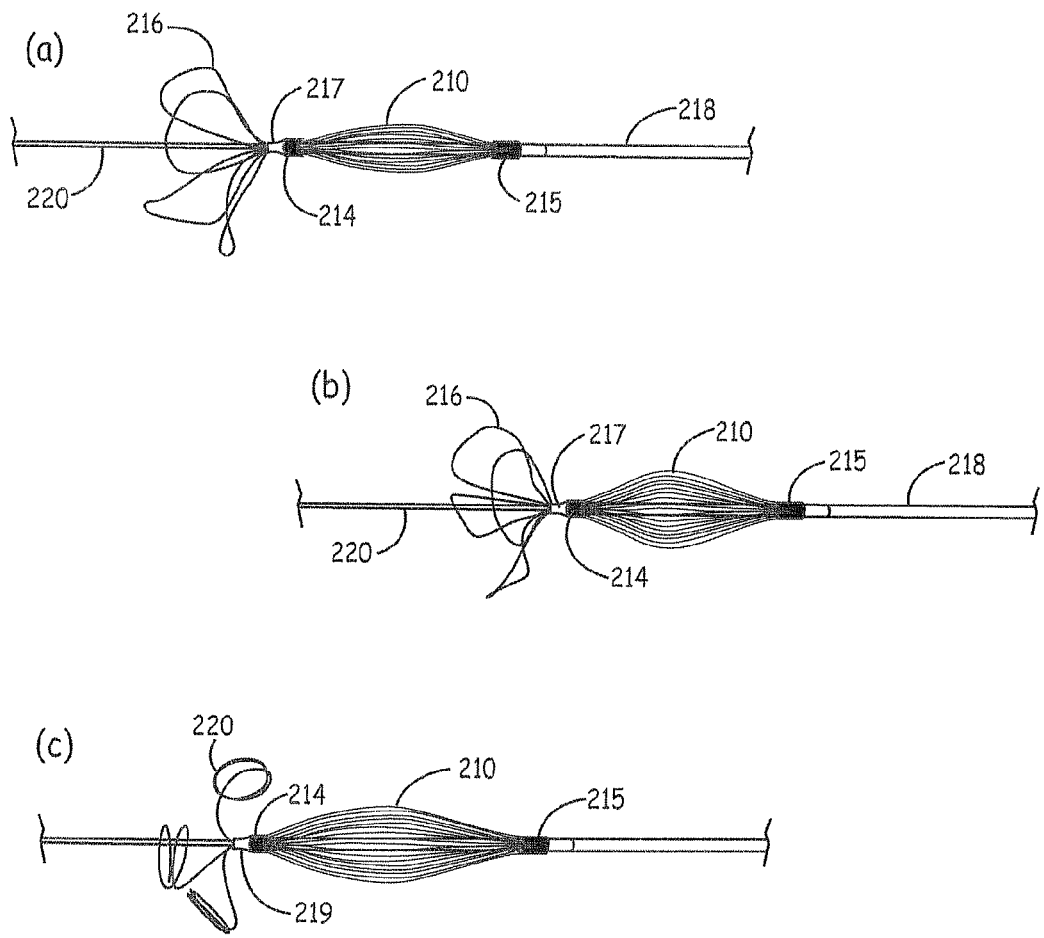
FIG. 9(a) is a fragmentary side view of a filter element in a reduced diameter delivery configuration coupled with a Nitinol frame supplemental engagement structure.
FIG. 9(b) is a fragmentary side view of the device of FIG. 9(a) with the filter element in a deployed configuration.
FIG. 9(c) is a fragmentary side view of an alternative Nitinol frame supplemental engagement structure with coiled Nitinol filaments upon release.

Referring to FIG. 9, a device comprising the filter element 210 and a Nitinol frame supplemental engagement structure is shown. The Nitinol frame supplemental engagement structure and the filter element can be integrally constructed within to resulting element or can be separate elements that are deployed adjacent each other. The device may be contained in a microcatheter in a reduced diameter delivery configuration in which the Nitinol elements are straightened for delivery. Once the microcatheter is released, the Nitinol frame expands into an extended deployment configuration as shown based on the shape memory of the metal. The filter element 210 shown in FIG. 9(a) is in a reduced diameter delivery configuration. The filter element 210 may be independently deployed into an extended configuration using a pushing element 218 and a view of the Nitinol frame supplemental engagement structure 216 with the filter element 210 deployed into an extended deployment configuration is shown in FIG. 9(b). The Nitinol frame supplemental engagement structure 216 comprises a plurality of Nitinol wires with one end of the wires secured at an attachment element 217. The attachment element 217 can be fixed or slidable on the delivery wire 220. The filter element 210 comprises a bundle of fibers with both ends of the fibers secured by fiber attachment elements 214 and 215. An alternative embodiment of the Nitinol frame is shown in FIG. 9(c) where Nitinol frame 220 comprises a plurality of Nitinol wires with one end of the wires secured at an attachment element 219. The Nitinol wires are coiled upon release in the vessel to reduce abrasion against a surrounding vessel.

Figure 10:
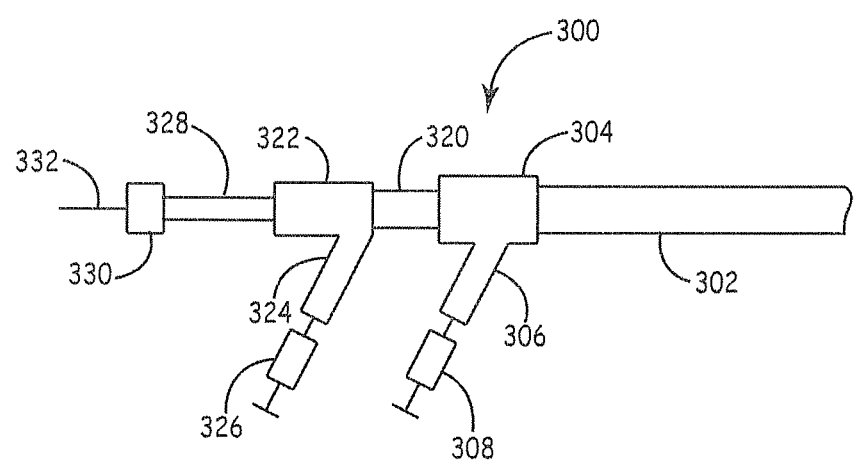
FIG. 10 is a fragmentary side view of the proximal end of a clot engagement system with appropriate fittings.

A representative configuration of the proximal end of the system that is manipulated outside of the patient is shown in FIG. 10. In general, the particular components vary based on the particular design selected and the order of use of the components. Referring to FIG. 10, the proximal end of a clot removal system 300 is shown. Guide catheter 302 provides a central lumen for the placement of other components of the system. A first touhy-borst fitting 304 is secured to the proximal end of guide catheter 302. First touhy-borst fitting 304 has a side arm 306 for the attachment of a fluid exchange element 308. Fluid exchange element 308 can be a syringe, pump or other appropriate fluid flow control device, which can be used to deliver a fluid, such as contrast dye or a medication, or to applied suction to remove liquid. In alternative embodiments, other suitable fittings can be used, and the fitting can comprise additional arms, such as embodiments with a first area for fluid delivery and a second arm for fluid withdrawal.

In the embodiment of FIG. 10, an optional aspiration catheter 320 is delivered through a valve of first fitting 304. As noted herein, aspiration can be performed with the guide catheter. The embodiment of FIG. 10 allows for aspiration through either or both of aspiration catheter 320 and guide catheter 302. Aspiration catheter 320 is shown with an over-the-wire configuration. Suitable rapid exchange aspiration catheters are described in published U.S. patent application 2007/0060944A to Boldenow et al., entitled "Tracking Aspiration Catheter," incorporated herein by reference.

Second touhy-borst fitting 322 is attached at the proximal end of aspiration catheter 320. Second touhy-borst fitting 322 has a side arm 324 for attachment to fluid aspiration device 326, which can be a syringe, pump or the like. Microcatheter 328 extends through a valve of second fitting 322. In some embodiments, any microcatheters used in the procedure are removed prior to the placement of a separate aspiration catheter, but in the embodiment of FIG. 10, both catheters are simultaneously loaded through guide catheter 302. Third fitting 330 is located at the proximal end of microcatheter 328. Flexible wire 332 extends from third fitting 330. Fiber-based clot engagement elements are generally supported on flexible wire 332. Suitable actuation tools or separate support structures for use with the fiber-based elements can be similarly delivered through the appropriate fitting.

Method of Using Embolectomy Devices

The procedure for clot removal generally comprises the delivery of the fiber-based clot engagement element in the vessel past the clot, pulling the clot in a proximal direction and aspirating the clot from the vessel. The process can further comprise breaking up the clot to facilitate clot removal. The clot engagement devices can generally comprise any of the structures described in the previous section. The procedure is designed to reduce or eliminate any release of fragments of the clot as emboli during the removal of the clot. Following removal of the clot, the fiber-based device is recovered, possibly with continued aspiration to limit or prevent release of fragments.

With respect to initial placement of the fiber-based structure, the element is presented past the clot. In some embodiments, the flexible wire can be directly delivered through the clot from a guide catheter within a carotid artery. In other embodiments, a microcatheter is first placed with its distal end past the clot, and the microcatheter can be delivered optionally over a guidewire, which can be placed with its distal tip past the clot. If a microcatheter is in place, the fiber-based element can be delivered through the microcatheter. Once a fiber-based element is in place past the clot, any additional fiber-based elements can be delivered to the desired location. An appropriate actuation element can then be used to deploy the fiber-based element.

Depending on the size of the clot and the corresponding aspiration catheter, it may or may not be convenient to aspirate the whole clot. In some embodiments, the clot can be drawn to the tip of the aspiration catheter and force against the aspiration catheter can be used to break up the clot for removal through the aspiration catheter. The use of the fiber-based element is particularly advantageous in this context since any emboli that break off from a fragmenting clot can be trapped by the fiber-based element for subsequent aspiration or removal through a guide catheter.

Figure 11:
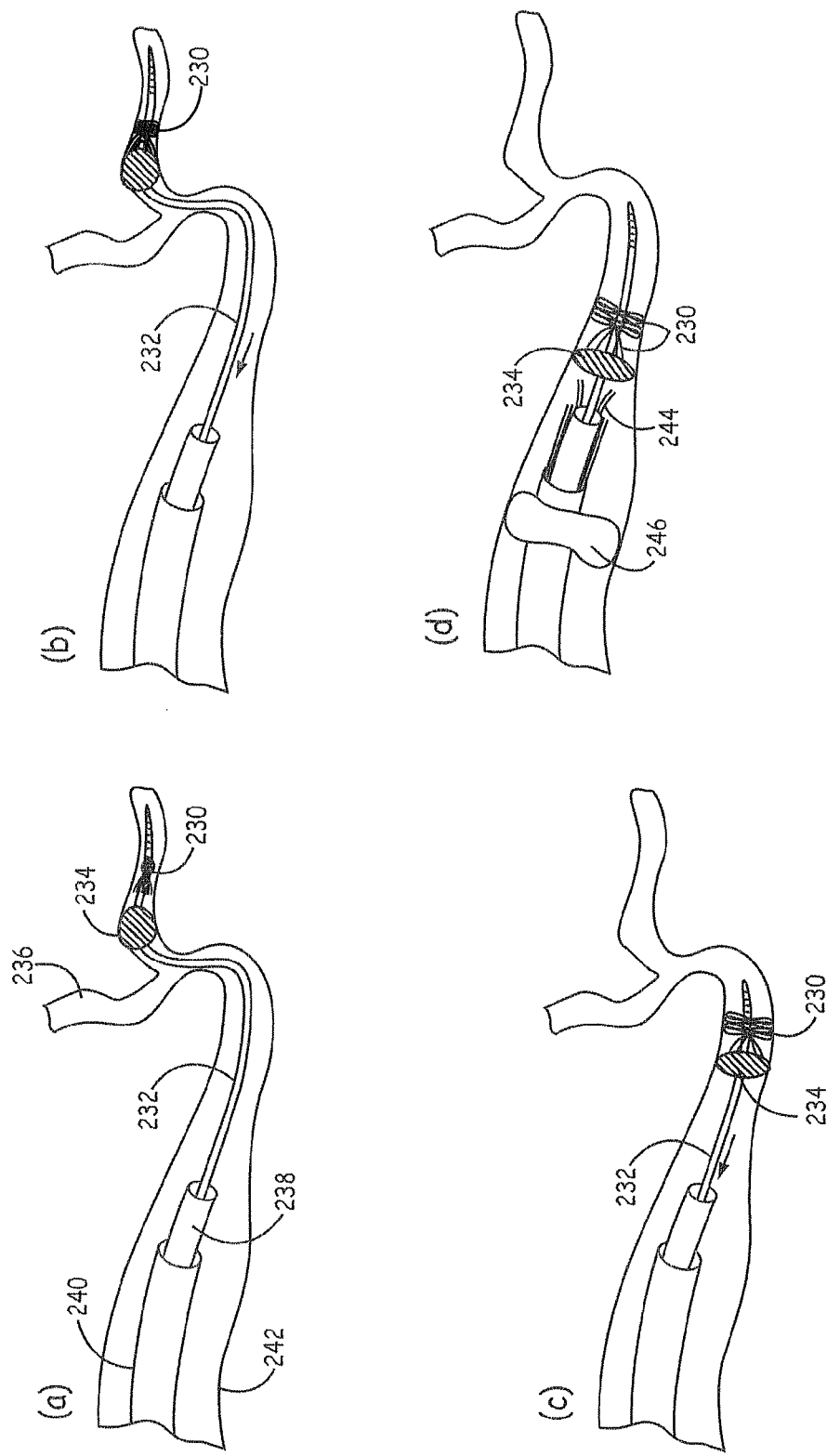
FIGS. 11(a)-(d) illustrates a process of a clot or emboli removal using an embodiment of the treatment device described herein.

Referring to FIG. 11, a process of clot removal using an embodiment of the treatment device is illustrated. FIG. 11(a) shows a filter element 230 at the distal portion of a delivery wire 232 is advanced cross a clot 234 in the cerebral artery 236. The placement of the filter element can be facilitated by monitoring the relative positions of the clot and a radio opaque band on the filter element. The delivery wire 232 is advance from a microcatheter 238, which resides inside the lumen of a guide catheter 240. The guide catheter is advanced in the carotid artery 242 close to the sharp bend in the cerebral artery. In some embodiments, the delivery wire with the filter element may be advanced pass the clot directly. Alternatively or additionally, a guide wire may optionally be used to facilitate the delivery of the filter element. Specifically, the guide wire can be first delivered across the clot. The microcatheter can then be advanced pass the clot over the guide wire. Once the microcatheter passes the clot, the guidewire is retrieved, and the delivery wire with the filter element is advanced pass the clot inside the microcatheter. The microcatheter can then be retrieved back to be close to the guide catheter.

FIG. 11(b) shows the filter element being deployed into a fiber mat distal to the clot. An optional actuation tool may be used to facilitate the deployment of the filter element. FIG. 11(c) shows the fiber mat retains the clot when the delivery wire is retrieved back towards the microcatheter. FIG. 11(d) shows when the clot is pulled close to the guide catheter, an optional occlusive balloon 246 can be deployed to temporarily block the blood flow or a portion thereof inside the vessel while suction 244 is being applied, and the delivery wire is being pulled back towards the microcatheter with the fiber mat. The clot 234, subjecting to both the pulling and/or the suction forces can be thus successfully removed. Any fragments that break off the clot can be controlled with the filter matrix and removed with suction or with the filter matrix. In some embodiments, when the clot is particularly hard, the clot engagement device can be pulled against the aspiration catheter to break up the clot to be removed by the aspiration.

Figure 12:
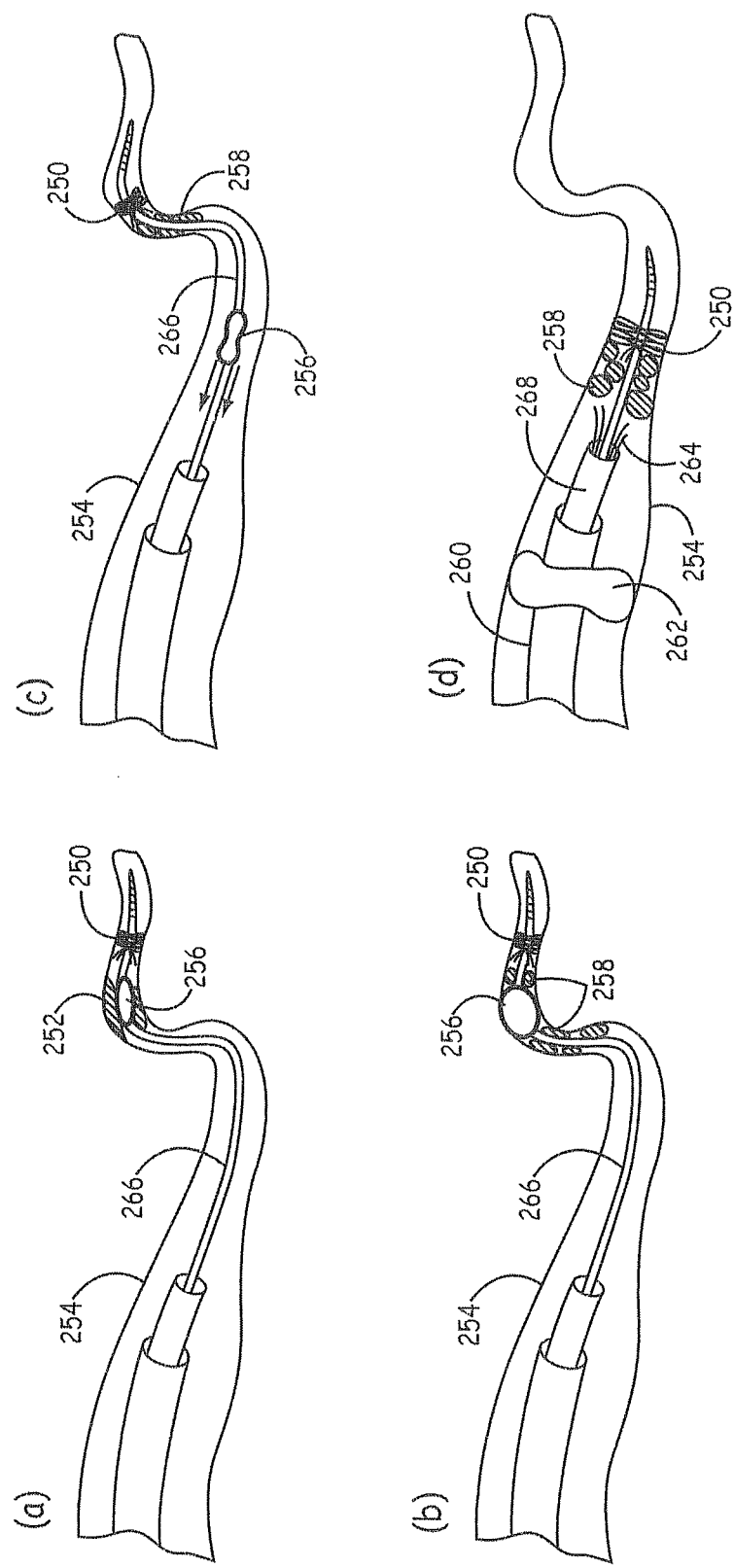
FIGS. 12(a)-(d) illustrates a process of a clot or emboli removal using an embodiment of the treatment device that has an angioplasty balloon.

Referring to FIG. 12, a process of a clot removal using an embodiment of the treatment device with an angioplasty balloon 256 is illustrated. FIG. 12(a) shows a filter element 250 in an extended deployed configuration distal to clot 252 in a vessel 254 with the balloon 256 being placed at the location of the clot. An optional actuation tool may be used to facilitate the deployment of the filter element. FIG. 12(b) shows the balloon 256 being deployed to dislodge the clot to form fragments 258. FIG. 12(c) shows the deployed fiber element 250 retains the dislodged clot fragments 258 while the deflated balloon 256 is being retrieved along the guidewire 266. FIG. 12(d) shows when the dislodged clot fragments 258 are pushed close to a guide catheter 260, an optional occlusive balloon 262 can be deployed to temporarily block the flow or a portion thereof inside the vessel while suction 264 is being applied, and the delivery wire 266 is being pulled back towards a microcatheter 268 with the deployed fiber element. The dislodged clot fragments 258, subjecting to both the pulling and/or the suction forces can be thus successfully removed.

Packaging and Distribution

The flexible wire and fiber-based elements of the clot engagement tool are generally packaged together in a sterile package. Suitable sterilization procedures are known in the art and other may be developed. Additional components of the overall system may or may not be packaged together. For example, depending on the design of the guide catheter, a conventional may be used, which could be packaged separately. Similar issues relate to other components of the overall system. In general, proprietary components used in the system may be packaged together for convenience.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. An acute stroke treatment device comprising a flexible delivery wire and a fiber-based clot engagement element that comprises at least one bundle of unwoven fibers, a first attachment element extending around the circumference of the flexible delivery wire wherein each fiber of the bundle is secured at one end to the first attachment element and wherein the bundle of fibers have a first low profile delivery configuration and a second extended, deployed configuration with a portion of the fibers flaring outward relative to the flexible delivery wire to have dimensions suitable to conform to the changing inner perimeter of a blood vessel, and an actuation tool that slides over the flexible delivery wire wherein the actuation tool is configured to engage the bundle to transition the fibers to the extended deployed configuration,
wherein the first attachment element either comprises a slide that can translate over the delivery wire or an anchor that is secured at a fixed position around the circumference of the delivery wire, and
wherein if the first attachment element has an anchor fixed to the delivery wire, the other end of the fibers are unsecured or are secured in a bundle at a second attachment element without fixed attachment to the actuation tool, and wherein if the first attachment element comprises a slide that can translate over the delivery wire, the other end of the fibers are unsecured or are attached to a second attachment element that can slide over the delivery wire.

2. The device of claim 1 wherein the unwoven fibers in the first configuration are substantially parallel to each other along the delivery wire in the bundle.

3. The device of claim 1 wherein the fibers in the second configuration form a three dimensional filtration matrix comprising effective pores with a distribution of sizes within the matrix while the fibers remain unwoven.

4. The device of claim 1 further comprising a radio-opaque band on the first attachment element.

5. The device of claim 1 wherein the fiber based element comprises a plurality of unwoven fiber bundles.

6. The device of claim 5 wherein a long non-woven fiber bundle is anchored at one or more positions along the fiber around the circumference of the flexible wire to form the plurality of fiber bundles that are inter-connected to each other.

7. The device of claim 5 wherein the plurality of fiber bundles each have its own attachment element.

8. The device of claim 5 wherein fiber bundles have one or both ends of the fibers secured.

9. The device of claim 1 further comprising heat shrink wrap around a portion of the fiber bundle such that the wrap forms a jacket around a portion of the fiber-based structure in the second configuration.

10. The device of claim 1 further comprising a supplemental engagement structure mounted or delivered on the flexible wire.

11. The device of claim 10 wherein the supplemental engagement structure is a filament structure comprising a plurality of polymeric filaments, wherein the polymeric filaments are substantially thicker than the fibers in the fiber bundle.

12. The device of claim 10 wherein the supplemental engagement structure is a Nitinol frame comprising a plurality of self-extendable Nitinol wires.

13. The device of claim 1 further comprising a mechanical treatment device delivered on the flexible wire.

14. The device of claim 13 wherein the mechanical treatment device is an atherectomy device, a stent, or an angioplasty balloon.

15. The device of claim 1 wherein the actuation tool is a microcatheter.

16. The device of claim 1 wherein the actuation tool comprises a filament cartridge comprising a plurality of filaments.

17. A system for the treatment of an acute stroke comprising:
the fiber based clot engagement element of claim 1,
wherein the actuation tool has a tubular distal end with an inner diameter such that the distal tip of the actuation tool slides over the delivery wire to deploy the fibers of the fiber-based clot engagement element to the second flared configuration; and
an aspiration catheter comprising a lumen with a distal opening in which the aspiration catheter can be delivered over the flexible delivery wire.

18. An acute stroke treatment device comprising a flexible delivery wire and a fiber-based clot engagement element that comprises a plurality of unwoven fiber bundles wherein each of the bundles of fibers have a first low profile delivery configuration and a second deployed configuration with a portion of the fibers that is unsecured flaring outward relative to the delivery wire to have dimensions suitable to conform to the changing inner perimeter of a blood vessel, a first attachment comprising a loop extending around the circumference of the delivery wire, a second attachment element comprising a loop extending around the circumference of the delivery wire, and an actuation tool that slides over the flexible delivery wire wherein the actuation tool is configured to engage the plurality of bundles of fibers to transition the fibers to the second deployed configuration,
wherein each fiber of a first bundle of the plurality of bundles is secured at one end to the first attachment element,
wherein each fiber of a second bundle of the plurality of bundles is secured at one end to the second attachment element and wherein the second attachment element can slide over the delivery wire without attachment to the actuation tool,
wherein the first attachment element either comprises a slide that can translate over the delivery wire or an anchor that is secured at a fixed position around the circumference of the delivery wire, and wherein if the first attachment element has an anchor fixed to the delivery wire, the other end of the fibers are unsecured or are secured in a bundle at a second attachment element without fixed attachment to the actuation tool.

19. The device of claim 18 wherein the unwoven fibers in the first configuration are substantially parallel to each other along the delivery wire in the bundle.

20. The device of claim 18 wherein the fibers in the second configuration form a three dimensional filtration matrix comprising effective pores with a distribution of sizes within the matrix while the fibers remain unwoven.

21. The device of claim 18 further comprising a radio-opaque band on the first attachment element.

22. The device of claim 18 wherein a long non-woven fiber bundle is anchored at one or more positions along the fiber around the circumference of the flexible wire to form the plurality of fiber bundles that are inter-connected to each other, wherein each of the plurality of fiber bundles has its own attachment element.

23. The device of claim 18 wherein fiber bundles have one or both ends of the fibers secured.

24. The device of claim 18 further comprising heat shrink wrap around a portion of the fiber bundle such that the wrap forms a jacket around a portion of the fiber-based structure in the second configuration.

25. The device of claim 18 further comprising a supplemental engagement structure mounted or delivered on the flexible wire.

26. The device of claim 25 wherein the supplemental engagement structure is a filament structure comprising a plurality of polymeric filaments, wherein the polymeric filaments are substantially thicker than the fibers in the fiber bundle.

27. The device of claim 25 wherein the supplemental engagement structure is a Nitinol frame comprising a plurality of self-extendable Nitinol wires.

28. The device of claim 18 further comprising a mechanical treatment device delivered on the flexible wire.

29. The device of claim 18 wherein the actuation tool is not fixedly attached to an attachment element securing fibers of a bundle.

30. The device of claim 29 wherein the actuation tool is a microcatheter.

31. The device of claim 18 wherein the first attachment element comprises a slide that can translate over the delivery wire.

32. The device of claim 1 wherein the first attachment element comprises a slide and the other end of the fibers are unsecured or are secured in a bundle at a second attachment element without fixed attachment to the actuation tool.

* * * * *